(12) United States Patent
Ansari

(10) Patent No.: US 11,807,547 B1
(45) Date of Patent: *Nov. 7, 2023

(54) METHOD FOR TREATING A BIOFILM

(71) Applicant: Imam Abdulrahman Bin Faisal University, Dammam (SA)

(72) Inventor: Mohammad Azam Ansari, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/337,112

(22) Filed: Jun. 19, 2023

Related U.S. Application Data

(63) Continuation of application No. 18/115,175, filed on Feb. 28, 2023, now Pat. No. 11,746,025, which is a continuation of application No. 17/329,987, filed on May 25, 2021, now Pat. No. 11,622,559.

(51) Int. Cl.
| | |
|---|---|
| *C01G 49/06* | (2006.01) |
| *A01N 59/20* | (2006.01) |
| *A61K 9/51* | (2006.01) |
| *A61K 33/34* | (2006.01) |
| *A61P 35/00* | (2006.01) |

(52) U.S. Cl.
CPC .............. *C01G 49/06* (2013.01); *A01N 59/20* (2013.01); *A61K 9/51* (2013.01); *A61K 33/34* (2013.01); *A61P 35/00* (2018.01); *C01P 2002/72* (2013.01); *C01P 2002/82* (2013.01); *C01P 2002/84* (2013.01); *C01P 2004/03* (2013.01); *C01P 2004/04* (2013.01); *C01P 2004/64* (2013.01); *C01P 2006/42* (2013.01)

(58) Field of Classification Search
CPC .......... C01G 49/06; A01N 59/20; A61K 9/51; A61K 33/34; A61P 35/00; C01P 2002/72; C01P 2002/82; C01P 2002/84; C01P 2004/03; C01P 2004/04; C01P 2004/64; C01P 2006/42

See application file for complete search history.

(56) References Cited

U.S. PATENT DOCUMENTS

2020/0030462 A1  1/2020  Sharad et al.

FOREIGN PATENT DOCUMENTS

IN   201841015633 A   5/2019

OTHER PUBLICATIONS

Mohammad Azam Ansari, et al., "Green synthesis, antimicrobial, antibiofilm and antitumor activities of superparamagnetic $\gamma$-Fe$_2$O$_3$ NPs and their molecular docking study with cell wall mannoproteins and peptidoglycan", International Journal of Biological Macromolecules, vol. 171, Feb. 28, 2021, pp. 44-58 (Abstract only).

S. Karlapudi, et al., "Bio Inspired Green Synthesis of Fe$_3$O$_4$ Magnetic Nanoparticles Using *Cassia Occidentalis* Leaves Extract and Efficient Catalytic Activity for Degradation of 4-Nitro Phenol", Der Pharmacia Lettre, vol. 10, No. 1, 2018, pp. 58-65.

Jyoti Singh, et al., "Therapeutic analysis of *Terminalia arjuna* plant extracts in combinations with different metal nanoparticles", Journal of Materials Nanoscience, vol. 2, No. 1, 2015, pp. 1-7.

Amrutha Lakshmi Konduru Ventaka, et al., "Synthesis of *Solanum nigrum* mediated copper oxide nanoparticles and their photocatalytic dye degradation studies", Materials Research Express, vol. 6, No. 12, Nov. 13, 2019, 3 pages (Abstract only).

F. Benakashani, et al., "Biosynthesis of silver nanoparticles using *Capparis spinosa* L. leaf extract and their antibacterial activity", Karbala International Journal of Modern Science, vol. 2, Issue 4, Dec. 2016, pp. 251-258.

Awatef M. Badrelden, et al., "Green synthesis of silver nanoparticles mediated extract of various in vitro plants (*Bacopa monnieri, Coleus blumei, Cichorium intybus*)", Bioscience Research, vol. 15, No. 1, 2018, pp. 1-11.

Bahar Khodadadi, et al., "*Achillea millefolium* L. extract mediated green synthesis of waste peach kernel shell supported silver nanoparticles: Application of the nanoparticles for catalytic reduction of a variety of dyes in water", Journal of Colloid and Interface Science, vol. 493, May 1, 2017, pp. 85-93 (Abstract only).

Mahmoud Nasrollahzadeh, et al., "*Tamarix gallica* leaf extract mediated novel route for green synthesis of CuO nanoparticles and their application for N-arylation of nitrogen-containing heterocycles under ligand-free conditions", RSC Advances, vol. 5, No. 51, 2015, pp. 40628-40635.

Laís Salomão Arias, et al., "Iron Oxide Nanoparticles for Biomedical Applications: A Perspective on Synthesis, Drugs, Antimicrobial Activity, and Toxicity", ANTIBIOTICS, vol. 7, No. 46, 2018, pp. 1-32.

(Continued)

*Primary Examiner* — Robert S Cabral
(74) *Attorney, Agent, or Firm* — Oblon, McClelland, Maier & Neustadt, L.L.P.

(57) ABSTRACT

A method of preparing iron oxide nanoparticles using an herbal mixture comprising *Capparis spinosa, Cichorium intybus, Solanum nigrum, Cassia occidentalis, Terminalia arjuna, Achillea millefolium,* and *Tamarix gallica*. The method produces crystalline $\gamma$-Fe$_2$O$_3$ nanoparticles which are superparamagnetic. The iron oxide nanoparticles are used in a method of killing or inhibiting the growth of a bacteria and/or fungus, particularly in the form of a biofilm. The nanoparticles are also used in a method of treating colon cancer.

15 Claims, 9 Drawing Sheets

(56) References Cited

OTHER PUBLICATIONS

P. Karnan, et al., "Green Biosynthesis of Magnetic Iron Oxide Nanoparticles of *Vitex Negundo* Aqueous Extract", International Journal of Current Pharmaceutical Research, vol. 10, Issue 3, 2018, pp. 11-14.
Eric C. Njagi, et al., "Biosynthesis of Iron and Silver Nanoparticles at Room Temperature Using Aqueous Sorghum Bran Extracts", LANGMUIR, vol. 27, No. 1, Dec. 6, 2010, pp. 264-271 (Abstract only).
Batool et al., Sci Rep 11, 22132 (2021). https://doi.org/10.1038/s41598-021-01374-4, pp. 1-9 (Year: 2021).
Turrina et al., Pharmaceuticals 2021, 14, 405. https://doi.org/10.3390/ph14050405, pp. 1-17. (Year: 2021).

FIG. 4A
FIG. 4B
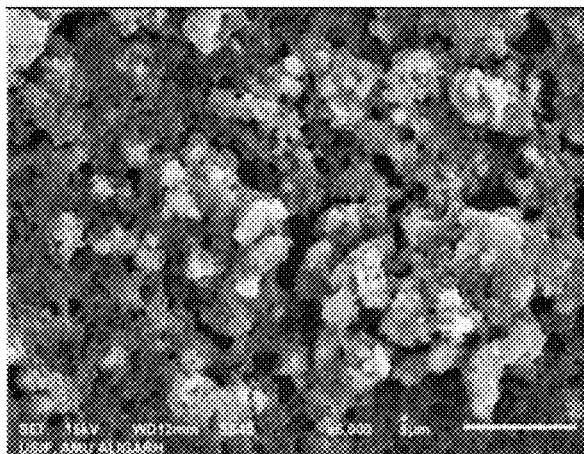
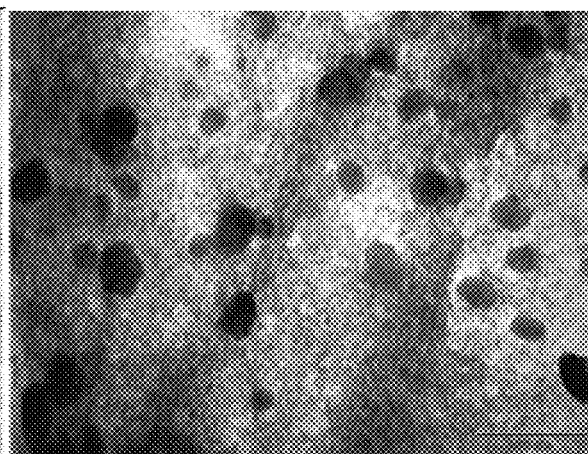
FIG. 4C
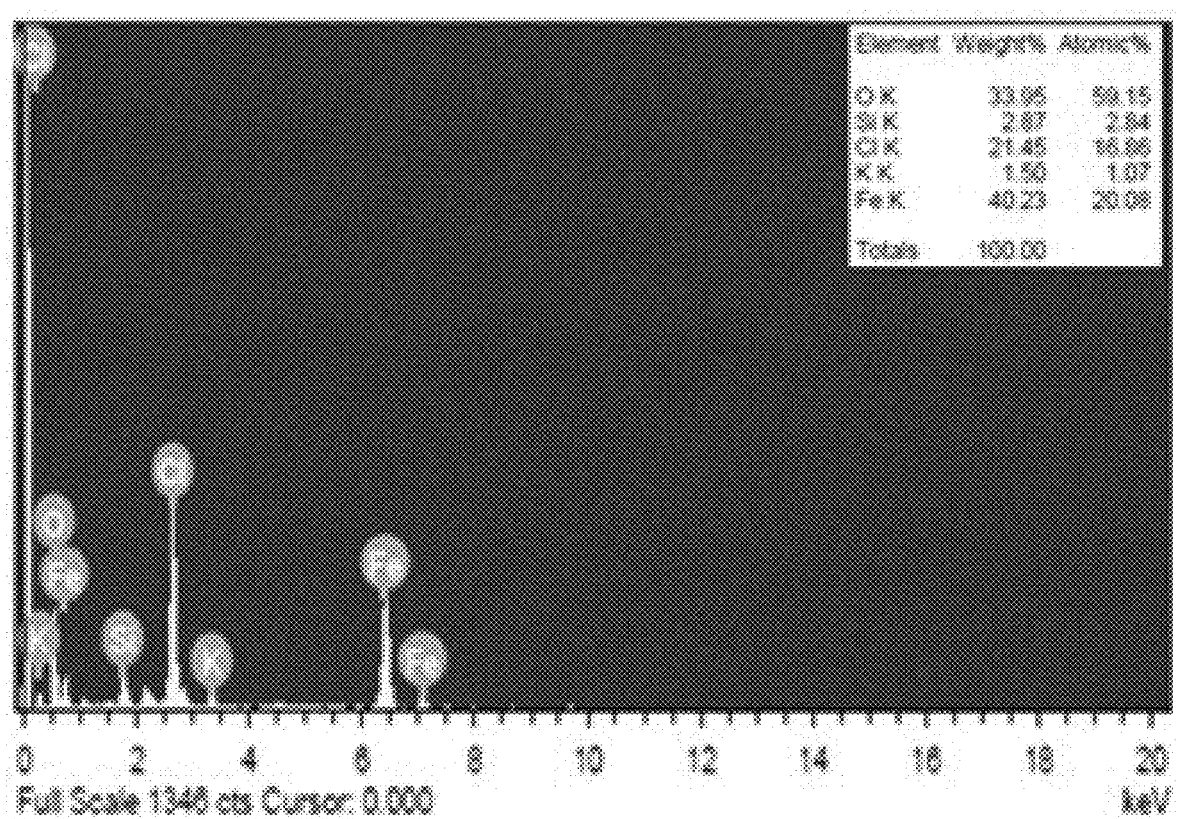

FIG. 9C
FIG. 9D
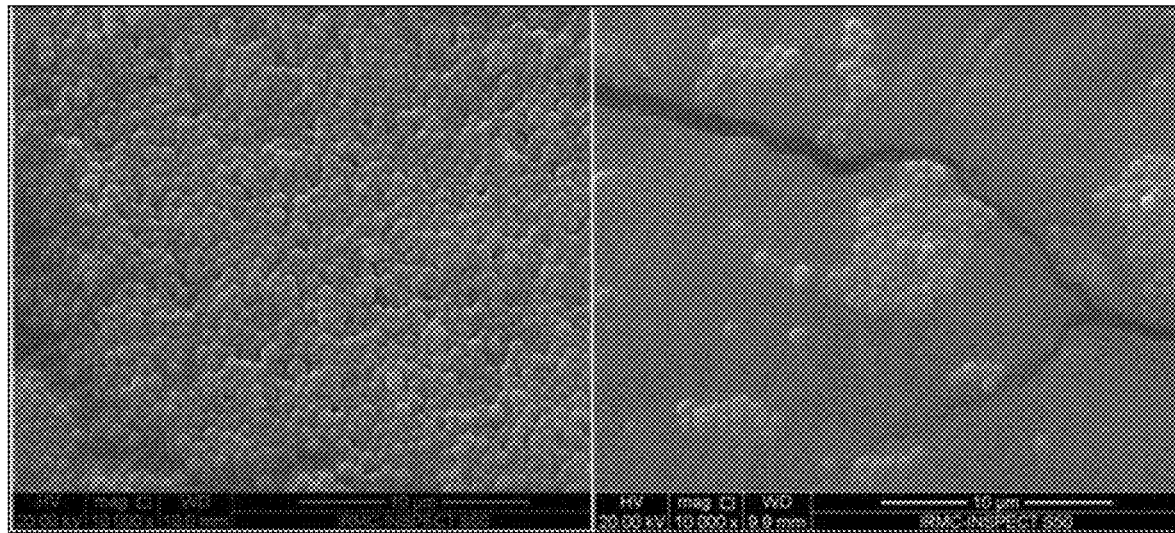
FIG. 9E
FIG. 9F
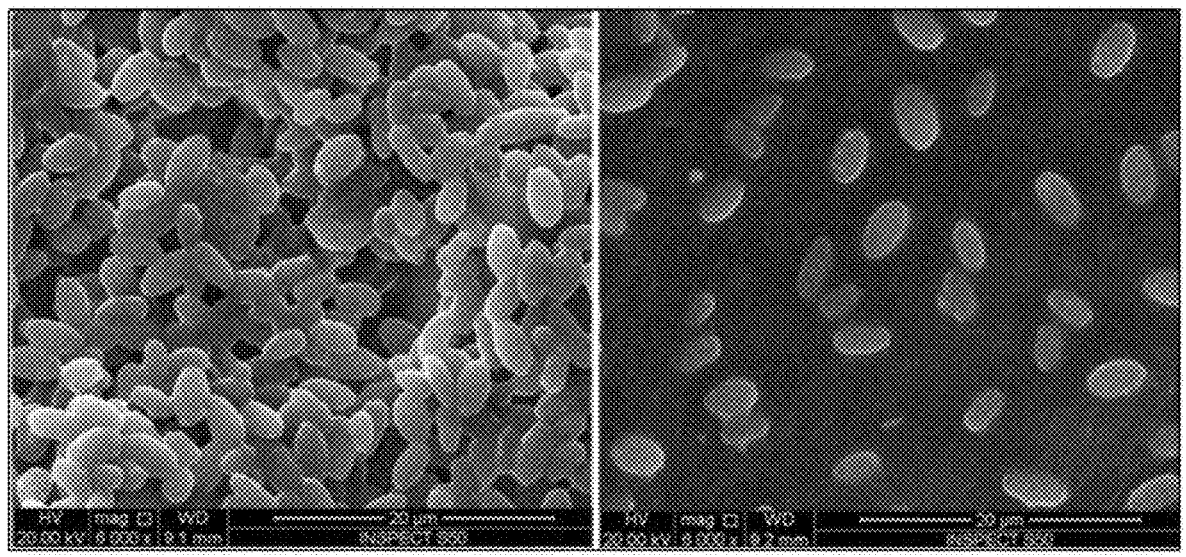

METHOD FOR TREATING A BIOFILM

CROSS-REFERENCE TO RELATED APPLICATIONS

The present application is a Continuation of U.S. application Ser. No. 18/115,175, now allowed, having a filing date of Feb. 28, 2023, which is a Continuation of U.S. application Ser. No. 17/329,987, now U.S. Pat. No. 11,622,559, having a filing date of May 25, 2021.

BACKGROUND OF THE INVENTION

Field of the Invention

The present disclosure relates to a method of preparing iron oxide nanoparticles with an extract of a plant mixture comprising *Capparis spinosa, Cichorium intybus, Solanum nigrum, Cassia occidentalis, Terminalia arjuna, Achillea millefolium*, and *Tamarix gallica*.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

The increasing emergence and re-emergence of antibiotic resistance in bacteria and *Candida* is a serious global concern for physicians, researchers and pharmaceutical industries. The infections caused by these drug resistant organisms are very difficult to diagnose and treat and thus cause increased morbidity and mortality compared to other infections.

Additionally, these organisms resistance to standard treatments causes serious problems when these organisms form biofilms. Biofilms are static complex microbial communities that can grow and form on surfaces of various kinds of medical devices and implants e.g., dental implants, catheters and sutures etc. [Sharma D, et. al., Antimicrobial Resistance & Infection Control. 2019; 8(1):76].

Biofilms comprise packed microbial populations held together by an extra-cellular matrix which is secreted by the microbes. The extra-cellular matrix is formed from materials such as exopolysaccharides, proteins, extracellular DNA and amyloidogenic proteins. Biofilm formation is a unique characteristic feature of a number of microbial species such as *Pseudomonas* species, *Staphylococcus* species, *Streptococcus* species, *Escherichia coli*, and *Candida* species. *Candida albicans* is an opportunistic fungal pathogen and is the major causative agent of oropharyngeal candidiasis, especially in immunocompromised patients [Salvatori 0, et. al., Journal of dental research. 2016; 95(4):365-71; and Jalal M, et. al., International journal of nanomedicine. 2019; 14:4667]. *C. albicans* biofilms structures are generally composed of multiple types of cells e.g., round budding yeast-form cells, elongated hyphal cells and oval pseudohyphal cells, which are encased in an extracellular matrix [Gulati M, et. al., Microbes and infection. 2016 May 1; 18(5):310-21]. *C. albicans* is the predominant yeast that has been isolated from medical device related infections e.g., pacemakers, joint prostheses, urinary and central venous catheters, heart valves, contact lenses, and dentures. In the United States, each year more than five million central venous catheters are placed and it has been found that biofilm infection occurs in more than 50% of these catheters [Fox E P, & Nobile C J. The role of *Candida albicans* biofilms in human disease. In: Dietrich L A, Friedmann T S, editors. *Candida albicans* symptoms, causes and treatment options. Nova Science Publishers; 2013. pp. 1-24]. Biofilms provide protection to the microorganism from various adverse environmental factors such as altered osmolarity and pH, nutrients paucity, and mechanical and shear forces. Additionally, biofilms also block the diffusion and penetration of antimicrobial agents inside the microbial biofilm communities. Thus, the biofilm extracellular matrix provides additional resistance strength to microbes which allows them to survive not only in harsh environments, but also makes them resistant to antimicrobial drugs which may lead to the emergence of multidrug-resistant, extensively drug-resistant, and totally drug-resistant bacteria [Stewart P S, International journal of medical microbiology. 2002; 292(2):107-13]. It has been reported that about 80% of chronic and recurrent microbial infections in the human body are due to microbial biofilms. Further, it has been reported that the microbial cells encased in biofilms matrix were 10-1000 times more antibiotics resistance than the planktonic cells [Mah T-F, Future Microbiol. 2012; 7:1061-72]. Therefore, disabling the biofilm formation by bacteria and *Candida* using unconventional antimicrobial agents such as nanoparticles may be an attractive alternative approach to treat and prevent the infection caused by these pathogenic bacteria and *Candida* species.

Recently, nanotechnology and nanomedicines have gained great attention as antimicrobial agents to combat infection caused by biofilm-forming or drug resistant bacteria and fungi. Significant research on antimicrobial potential of various types of nanoparticles has been reported in the literature against different bacterial and fungal strains including Ag nanoparticles [Jalal M, et. al., International Journal of Advanced Research. 2016; 4(12):428-40; Ali S G, et. al., In Silico Pharmacology. 2017; 5(1):12; and Almatroudi A, et. al., Processes. 2020; 8(4):388], Au nanoparticles [Ali S G, et. al., Antibiotics. 2020; 9(3):100], ZnO nanoparticles [Sultan A, et. al., Int. J. Curr. Microbiol. App. Sci. 2015; 1:38-47; Ali S G, et. al., Antibiotics. 2020; 9(5):260; and Prasad K S, et. al., Biomolecules. 2020; 10(7):982], and Cu nanoparticles [Thiruvengadam M, et. al., Bioprocess and biosystems engineering. 2019; 42(11):1769-77]. These nanoparticles, however, are not without drawbacks. For example, while Ag nanoparticles have shown antimicrobial activity against a large number of bacterial and fungal species, they have also been shown to exhibit toxicity in zebrafish [Asharani P V, et. al., Nanotechnology. 2008; 19(25):255102], Crucian carp, Eurasian perch [Bilberg K, et. al., Aquat Toxicol. 2011; 104(1):145-52], in various human cell lines [Kawata K, et. al., Environ Sci Technol. 2009; 43(15):6046-51; and Foldbjerg R, et. al., Arch Toxicol. 2011; 85(7):743-50] and in vivo in mice [Ansari M A, et. al., Environmental toxicology. 2016; 31(8):945-56].

Therefore, an ideal microbiocidal agent should be toxic to bacteria and fungi, but safe to human cells. One such candidate is iron and its compounds. Iron oxide NPs (IONPs) have been shown to be non-toxic [Samanta B, et. al., J Mater Chem. 2008; 18(11):1204-8; Sun C, et. al., ACS Nano. 2010; 4(4):2402-10; and Prodan A M, et. al., J Nanomater. 2013; 2013: 587021]. Further, iron oxide nanoparticle can degraded by natural body processes and can act as a supplementary iron source [Weissleder R, et. al., Am J Roentgenol. 1989; 152(1):167-73]. The IONPs have been shown to inhibit growth of *Staphylococcus aureus, Escherichia coli* [Darwish M S A, et. al., J Nanomater. 2015;

2015:416012], *Bacillus subtillis* and *P. aeruginosa* [Farouk F, et. al., Biotechnology Letters. 2020; 42(2):231-40], prevent biofilm formation by *P. aeruginosa* [Armijo L M, et. al., Journal of Nanobiotechnology. 2020; 18(1):1-27] and *S. aureus* [Shi S F, et. al., International journal of nanomedicine. 2016; 11: 6499].

While many methods have been used for synthesizing iron oxide nanoparticles, "green" approaches for NPs synthesis have several advantages: they are eco-friendly, cost-effective, facile, non-toxic, and rapid and most importantly additional chemical capping and stabilization agents not required. One such green approach is the use of plants or plant extracts as reducing or stabilizing/capping agents for nanoparticles. Additionally, many herbal plants, their parts, and their products have themselves been used for the treatment of various kinds of diseases.

Accordingly, the present disclose describes a method of preparing iron oxide nanoparticles using an extract of a plant mixture. The method produces iron oxide nanoparticles which may be stabilized or capped by phytochemicals which are present in the plant mixture. These iron oxide nanoparticles with the phytochemical stabilizing/capping agents are useful as antimicrobial agents and in colon cancer treatment.

SUMMARY OF THE INVENTION

The present disclosure relates to a method of preparing iron oxide nanoparticles, the method comprising mixing an iron precursor solution comprising an iron (III) salt and a solvent with an extract of a plant mixture to form a reaction mixture, heating the reaction mixture to form the iron oxide nanoparticles, and isolating the iron oxide nanoparticles, wherein the plant mixture comprises *Capparis spinosa, Cichorium intybus, Solanum nigrum, Cassia occidentalis, Terminalia arjuna, Achillea millefolium,* and *Tamarix gallica.*

In some embodiments, the method further comprises soaking the plant mixture in water in an amount of 1 g of plant mixture per 1 to 25 mL of water at 5 to 50° C. for 4 to 48 hours to form a plant suspension, and filtering the plant suspension to form the extract.

In some embodiments, the plant mixture comprises 26 to 27.5 wt % *Capparis spinosa,* 26 to 27.5 wt % *Cichorium intybus,* 12.5 to 14 wt % *Solanum nigrum,* 6 to 7 wt % *Cassia occidentalis,* 12.5 to 14 wt % *Terminalia arjuna,* 6 to 7 wt % *Achillea millefolium,* and 6 to 7 wt % *Tamarix gallica.*

In some embodiments, the solvent is water, the iron (III) salt is an iron (III) halide, and the heating is performed at 40 to 80° C. for 15 to 180 minutes.

In some embodiments, the reaction mixture has an iron (III) concentration of 0.25 to 1.25 mM and the extract is present in the reaction mixture in an amount of 24 to 120 mL extract per mmol of iron (III).

In some embodiments, the iron oxide nanoparticles comprise crystalline $\gamma$-$Fe_2O_3$ by PXRD and a mean particle size of 10 to 100 nm by electron microscopy.

In some embodiments, the iron oxide nanoparticles have a saturation magnetization of 17.5 to 27.5 emu/g and a coercivity less than 250 Oe at 275 to 325 K.

The present disclosure also relates to iron oxide nanoparticles, comprising iron oxide stabilized with an extract of a plant mixture comprising *Capparis spinosa, Cichorium intybus, Solanum nigrum, Cassia occidentalis, Terminalia arjuna, Achillea millefolium,* and *Tamarix gallica.*

In some embodiments, the iron oxide nanoparticles comprise crystalline $\gamma$-$Fe_2O_3$ by PXRD.

In some embodiments, the iron oxide nanoparticles have a mean particle size of 10 to 100 nm by electron microscopy.

In some embodiments, the iron oxide nanoparticles have a saturation magnetization of 17.5 to 27.5 emu/g and a coercivity less than 250 Oe at 275 to 325 K.

In some embodiments, the plant mixture comprises 26 to 27.5 wt % *Capparis spinosa,* 26 to 27.5 wt % *Cichorium intybus,* 12.5 to 14 wt % *Solanum nigrum,* 6 to 7 wt % *Cassia occidentalis,* 12.5 to 14 wt % *Terminalia arjuna,* 6 to 7 wt % *Achillea millefolium,* and 6 to 7 wt % *Tamarix gallica.*

In some embodiments, the extract comprises at least three selected from the group consisting of: n-hexadecanoic acid, (Z,Z)-9,12-octadecadienoic acid, (Z)-9-octadecenoic acid, octadecanoic acid, (Z)-3-(pentadec-8-en-1-yl)phenol, piperine, 2-(hydroxymethyl)-2-nitro-1,3-propanediol, and tetradecanoic acid.

In some embodiments, the extract further comprises at least one selected from the group consisting of: quercetin, kaempferol, cappariloside A, capparine A, capparine B, capparisine A, capparisine B, capparisine C, lactucin, lactucopicrin, aesculetin, aesculin, cichoriin, umbelliferone, scopoletin, 6,7-dihydrocoumarin, solasodine, solanine, emodin, cassiollin, *cassia* occidentanol I, *cassia* occidentanol II, arjunin, arjunic acid, arjungenin, arjunetin, arjunone, arjunoside I, arjunoside II, arjunoside III, arjunoside IV, archilletin, achilleine, apigenin, luteolin, tamarixin, tamarixetin, 4-methylcoumarin, and troupin.

The present disclosure also relates to a method of killing or inhibiting the growth of bacteria and/or fungus, the method comprising exposing the bacteria and/or fungus to the iron oxide nanoparticles.

In some embodiments, the bacteria and/or fungus is in the form of a biofilm.

In some embodiments, the bacteria and/or fungus is at least one selected from the group consisting of *P. aeruginosa, S. aureus,* and *C. albicans.*

In some embodiments, the iron oxide nanoparticles have a minimum inhibitory concentration (MIC) for *P. aeruginosa* of 0.60 to 1.5 mg iron oxide nanoparticles per mL, a MIC for *S. aureus* of 0.9 to 2.45 mg iron oxide nanoparticles per mL, and a MIC for *C. albicans* of 1.30 to 2.85 mg iron oxide nanoparticles per mL.

The present disclosure also relates to a method of treating colon cancer, the method comprising administering to a patient in need of therapy an effective dose of the iron oxide nanoparticles.

In some embodiments, the iron oxide nanoparticles are administered in an amount sufficient to provide a concentration of 15 to 200 μg iron oxide nanoparticles per mL of tumor volume at a colon cancer-containing site.

BRIEF DESCRIPTION OF THE DRAWINGS

FIGS. 4A-4D show electron microscopy characterization of the synthesized iron oxide nanoparticles where FIG. 4A is a scanning electron microscopy image of the iron oxide nanoparticles, FIG. 4B is a transmission electron microscopy image of the iron oxide nanoparticles, FIG. 4C is a selected area EDX spectrum of the iron oxide nanoparticles, and FIG. 4D is a size histogram of the iron oxide nanoparticles derived from the electron microscopy images;

FIGS. 7A-7F are scanning electron microscopy images of bacteria and fungus where FIG. 7A shows *P. aeruginosa* before exposure to the iron oxide nanoparticles, FIG. 7B shows *P. aeruginosa* after exposure to the iron oxide nanoparticles, FIG. 7C shows MRSA before exposure to the iron oxide nanoparticles, FIG. 7D shows MRSA after exposure to the iron oxide nanoparticles, FIG. 7E shows *C. albicans* before exposure to the iron oxide nanoparticles, and FIG. 7F shows *C. albicans* after exposure to the iron oxide nanoparticles;

FIGS. 9A-9F are scanning electron microscopy images of biofilms of bacteria and fungus where FIG. 9A shows a biofilm of *P. aeruginosa* before exposure to the iron oxide nanoparticles, FIG. 9B shows a biofilm of *P. aeruginosa* after exposure to the iron oxide nanoparticles, FIG. 9C shows a biofilm of MRSA before exposure to the iron oxide nanoparticles, FIG. 9D shows a biofilm of MRSA after exposure to the iron oxide nanoparticles, FIG. 9E shows a biofilm of *C. albicans* before exposure to the iron oxide nanoparticles, and FIG. 9F shows a biofilm of *C. albicans* after exposure to the iron oxide nanoparticles;

DETAILED DESCRIPTION OF THE INVENTION

Figure 1:
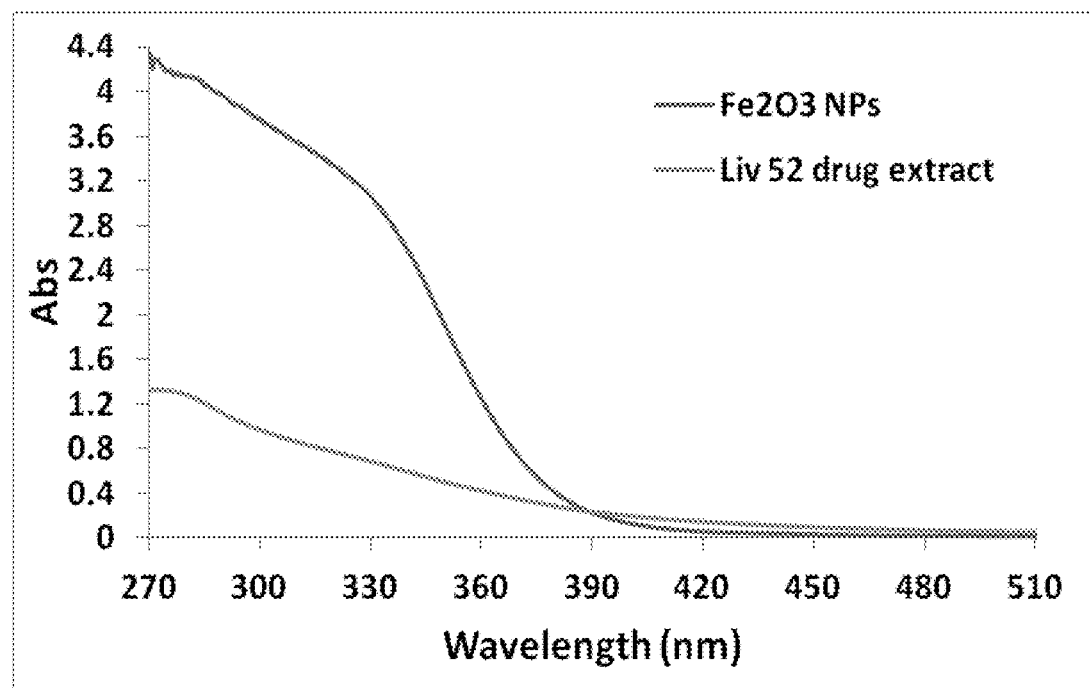
FIG. 1 shows UV-vis spectra of the extract of the plant mixture and the synthesized iron oxide nanoparticles.

In the following description, it is understood that other embodiments may be utilized and structural and operational changes may be made without departure from the scope of the present embodiments disclosed herein.

Definitions

As used herein the words "a" and "an" and the like carry the meaning of "one or more."

As used herein, the terms "optional" or "optionally" means that the subsequently described event(s) can or cannot occur or the subsequently described component(s) may or may not be present (e.g., 0 wt. %).

According to a first aspect, the present disclosure relates to a method of preparing iron oxide nanoparticles, the method comprising mixing an iron precursor solution comprising an iron (III) salt and a solvent with an extract of a plant mixture to form a reaction mixture, heating the reaction mixture to form the iron oxide nanoparticles, and isolating the iron oxide nanoparticles. The plant mixture used in this method comprises *Capparis spinosa* (also referred to as caper bush and Finders rose), *Cichorium intybus* (also referred to as chicory or common chicory), *Solanum nigrum* (also referred to as European black nightshade, black nightshade, and blackberry nightshade), *Cassia occidentalis* (also referred to as *senna occidentalis*, 'au'auko'i, septicweed, coffee *senna*, coffeeweed, Mogdad coffee, negro-coffee, *senna* coffee, Stephanie coffee, stinkingweed, styptic weed, and bana chakunda), *Terminalia arjuna* (also referred to as arjuna or Arjun tree), *Achillea millefolium* (also referred to as yarrow or common yarrow), and *Tamarix gallica* (also referred to as French tamarisk). The plant mixture is also referred to as Liv52™ available from The Himalaya Drug Company (Himalaya).

In general, the plant mixture may contain the plants listed above in any relative amounts. In preferred embodiments, the plant mixture comprises 26 to 27.5 wt %, preferably 26.5 to 27.25 wt %, preferably 26.75 to 27.0 wt %, preferably 26.8 to 26.9 wt % *Capparis spinosa*, 26 to 27.5 wt %, preferably 26.5 to 27.25 wt %, preferably 26.75 to 27.0 wt %, preferably 26.8 to 26.9 wt % *Cichorium intybus*, 12.5 to 14 wt %, preferably 12.75 to 13.75 wt %, preferably 12.8 to 13.7 wt %, preferably 12.9 to 13.6 wt %, preferably 13 to 13.5 wt %, preferably 13.1 to 13.4 wt %, preferably 13.2 to 13.3 wt % *Solanum nigrum*, 6 to 7 wt %, preferably 6.25 to 6.9 wt %, preferably 6.4 to 6.8 wt %, preferably 6.6 to 6.7 wt % *Cassia occidentalis*, 12.5 to 14 wt %, preferably 12.75 to 13.75 wt %, preferably 12.8 to 13.7 wt %, preferably 12.9 to 13.6 wt %, preferably 13 to 13.5 wt %, preferably 13.1 to 13.4 wt %, preferably 13.2 to 13.3 wt % *Terminalia arjuna*, 6 to 7 wt %, preferably 6.25 to 6.9 wt %, preferably 6.4 to 6.8 wt %, preferably 6.6 to 6.7 wt % *Achillea millefolium*, and 6 to 7 wt %, preferably 6.25 to 6.9 wt %, preferably 6.4 to 6.8 wt %, preferably 6.6 to 6.7 wt % *Tamarix gallica*.

Liv 52 is a polyherbal ayurvedic medicinal formulation of *Capparis spinosa* (130 mg), *Cichorium intybus* (130 mg), *Solanum nigrum* (64 mg), *Cassia occidentalis* (32 mg), *Terminalia arjuna* (64 mg), *Achillea millefolium* (32 mg), and *Tamarix gallica* (32 mg) plants, and is most commonly prescribed as a traditional hepatotonic for the treatment of liver cirrhosis and viral hepatitis in India. The formulation is used to, for example, stimulate appetite and protect the liver against hepatotoxins (i.e., beryllium, CCl4, paracetamol, alcohol) [De Silva H A, et. al., J Ethnopharmacol. 2003; 84(0:47-50]. Further, herbs and herbal mixture such as Liv 52 possess large amounts of polyphenolic and long-chain saturated and unsaturated fatty acid which may act as reducing, stabilising and capping agents for nanoparticles.

In general, any part or combination of parts of the plants listed above may be used in the extract used in the current invention. For example, the extract may be made using whole plants, roots, stems, leaves, flowers, bark, bulbs, fruits, seeds, buds, or any combination thereof. In some embodiments, the extract of the plant mixture comprises a whole plant extract of one or any combination of the plants listed above. In some embodiments, the extract of the plant mixture comprises a root extract of one or any combination of the plants listed above. In some embodiments, the extract of the plant mixture comprises a stem extract of one or any combination of the plants listed above. In some embodiments, the extract of the plant mixture comprises a leaf extract of one or any combination of the plants listed above. In some embodiments, the extract of the plant mixture comprises a flower extract of one or any combination of the plants listed above. In some embodiments, the extract of the plant mixture comprises a bark extract of one or any combination of the plants listed above. In some embodiments, the extract of the plant mixture comprises a bulb extract of one or any combination of the plants listed above. In some embodiments, the extract of the plant mixture comprises a fruit extract of one or any combination of the plants listed above. In some embodiments, the extract of the plant mixture comprises a seed extract of one or any combination of the plants listed above. In some embodiments, the extract of the plant mixture comprises a bud extract of one or any combination of the plants listed above. In general, the plant mixture may be prepared for making the extract by any suitable technique known to one of ordinary skill in the art. For example, the plant mixture or any component thereof may be dried before making the extract and/or reduced in size to small particles. In general, the plant mixture or any component thereof may be reduced to small particles using any suitable technique known to one of ordinary skill in the art. Examples of such techniques include, but are not limited to milling, grinding, ball milling, chopping, pulverizing, crushing, pounding, mincing, shredding, smashing, and fragmenting. In some embodiments, the reducing to small particles may take place using a mill, ball mill, rod mill, autogenous mill, semi-autogenous grinding mill, pebble mill, buhrstone mill, burr mill, tower mill, vertical shaft impactor mill, a low energy milling machine, grinder, pulverizer, mortar and pestle, blender, crusher, or other implement used to reduce a material to small particles.

In general, the extract of the plant mixture may be prepared by any suitable method known to one of ordinary skill in the art. Such a method may involve, for example, plant tissue homogenization, soaking, maceration, digestion, decoction, infusion, percolation, Soxhlet extraction, superficial extraction, ultrasound-assisted, microwave-assisted extraction, or any combination thereof. In some embodiments, the plant mixture is prepared by soaking. The soaking may or may not involve agitation, such as shaking or stirring. In general, any suitable solvent known to one of ordinary skill in the art may be used to prepare the extract of the plant mixture. Examples of such suitable solvents include, but are not limited to hexane, petroleum ether, diethyl ether, ethyl acetate, chloroform, dichloromethane, acetone, n-butanol, isopropanol, n-propanol, ethanol, methanol, water, and mixtures thereof. In some embodiments, the solvent comprises water. In preferred embodiments, the solvent is water. In general, the plant mixture may be used in any suitable amount known to one of ordinary skill in the art to prepare the extract. In some embodiments, the extract is prepared at a concentration (which may be measured by the amount of plant mixture per volume of solvent) at which it is intended to be used. In alternative embodiments, the extract is not prepared at a concentration at which it is intended to be used. In such embodiments, a concentration of the extract may be adjusted before use in the method of preparing iron oxide nanoparticles. Such adjustment may be made by any suitable method known to one of ordinary skill in the art. In some embodiments, the extract is diluted to a lower concentration compared to a preparation concentration for use in the method of preparing iron oxide nanoparticles. In alternative embodiments, the extract is concentrated, for example by evaporation, to a higher concentration compared to the preparation concentration for use in the method of preparing iron oxide nanoparticles. In some embodiments, the extract is prepared using 1 g of plant mixture per 1 to 25 mL, preferably 2.5 to 20 mL, preferably 5 to 15 mL, preferably 7.5 to 12.5 mL, preferably 8 to 12 mL, preferably 9 to 11 mL, preferably 10 mL of solvent. In some embodiments, the soaking is performed at 5 to 50° C., preferably 10 to 40° C., preferably 15 to 35° C., preferably 20 to 30° C., preferably 22.5 to 27.5° C., preferably about 25° C. In some embodiments, the soaking is performed for 4 to 48 hours, preferably 6 to 44 hours, preferably 8 to 40 hours, preferably 10 to 36 hours, preferably 12 to 32 hours, preferably 14 to 28 hours, preferably 16 to 24 hours. This soaking creates a plant suspension which comprises a liquid solvent extract and suspended plant solids. In preferred embodiments, the plant solids are removed following the soaking. In general, the plant solids may be removed by any suitable technique known to one of ordinary skill in the art. Examples of such suitable techniques include, but are not limited to decantation, centrifugation, and filtration, but excluding techniques such as evaporation and distillation. In preferred embodiments, the method further comprises soaking the plant mixture in water in an amount of 1 g of plant mixture per 1 to 25 mL, preferably 2.5 to 20 mL, preferably 5 to 15 mL, preferably 7.5 to 12.5 mL, preferably 8 to 12 mL, preferably 9 to 11 mL, preferably 10 mL of water at 5 to 50° C., preferably 10 to 40° C., preferably 15 to 35° C., preferably 20 to 30° C., preferably 22.5 to 27.5° C., preferably about 25° C. for 4 to 48 hours, preferably 6 to 44 hours, preferably 8 to 40 hours, preferably to 36 hours, preferably 12 to 32 hours, preferably 14 to 28 hours, preferably 16 to 24 hours to form a plant suspension, and filtering the plant suspension to form the extract.

In general, the iron (III) salt may be any suitable iron (III) salt known to one of ordinary skill in the art. Examples of such suitable iron (III) salts include, but are not limited to iron (III) nitrate, iron (III) acetate, iron (III) halides including iron (III) chloride, iron (III) bromide, and iron (III) iodide, iron (III) sulfate, iron (III) oxalate, iron (III) phosphate, iron (III) gluconate, iron (III) fumarate, iron (III) citrate, and iron (III) chromate. In preferred embodiments, the iron (III) salt is an iron (III) halide. In some embodiments, the iron (III) halide is iron (III) chloride. In general, the solvent may be any suitable solvent known to one of ordinary skill in the art. Examples of such suitable solvents include but are not limited to hexane, petroleum ether, diethyl ether, ethyl acetate, chloroform, dichloromethane, acetone, n-butanol, isopropanol, n-propanol, ethanol, methanol, water, acetaldehyde, acetic acid, acetonitrile, 1,2-butanediol, 1,3-butanediol, 1,4-nutanediol, 2-butoxyethanol, butyric acid, diethanolamine, diethylenetriamine, dimethylformamide, dimethoxyethane, dimethyl sulfoxide, 1,4-dioxane, ethylamine, ethylene glycol, formic acid, furfuryl alcohol, glycerol, methyl diethanolamine, methyl isocyanide, N-methyl-2-pyrrolidone, 1,3-propanediol, 1,5-pentanediol, propanoic acid, propylene glycol, pyridine, tetrahydrofuran, triethylene glycol, diglyme, and mixtures thereof. In some embodiments, the solvent comprises water. In some embodiments, the solvent is water. In some embodiments, the heating is performed at 40 to 80° C., preferably 50 to 75° C., preferably 60 to 70° C., preferably 65° C. In some embodiments, the heating is performed for 15 to 180 minutes, preferably 30 to 120 minutes, preferably 45 to 90 minutes, preferably 50 to 70 minutes, preferably 55 to 65 minutes, preferably 60 minutes. Following the heating, the iron oxide nanoparticles may be collected or isolated. In general, the iron oxide nanoparticles may be collected or isolated by any suitable technique known to one of ordinary skill in the art. Examples of such techniques include, but are not limited to, liquid-liquid extraction, dialysis, centrifugation, chromatography, precipitation, filtration, and decantation. In some embodiments, the collecting or isolating comprises washing. In general, the washing may be performed using any suitable technique known to one of ordinary skill in the art. In some embodiments, the washing is performed with a wash solvent which may be any suitable solvent as described above. In some embodiments, multiple rounds of washing are performed. These multiple rounds may be performed with the same wash solvent or with different wash solvents. In some embodiments, the solvent is water, the iron (III) salt is an iron (III) halide, and the heating is performed at 40 to 80° C. for 15 to 180 minutes.

In some embodiments, the reaction mixture has an iron (III) concentration of 0.25 to 1.25 mM, preferably 0.3 to 1.2 mM, preferably 0.4 to 1.1 mM, preferably 0.5 to 1.0 mM, preferably 0.55 to 0.9 mM, preferably 0.6 to 0.8 mM, preferably 0.65 to 0.75 mM. In some embodiments, extract is present in the reaction mixture in an amount of 24 to 120 mL extract per mmol of iron (III), preferably 25 to 100 mL, preferably 30 to 75 mL, preferably 32.5 to 60 mL, preferably 35 to 55 mL, preferably 37.5 to 50 mL, preferably 40 to 45 mL, preferably 41 to 44, preferably 42 to 43 mL extract per mmol of iron (III). In some embodiments, the reaction mixture has an iron (III) concentration of 0.25 to 1.25 mM and the extract is present in the reaction mixture in an amount of 24 to 120 mL extract per mmol of iron (III).

In some embodiments, the reaction mixture further comprises a supplementary reducing agent. In general, the supplementary reducing agent may be any suitable reducing agent known to one of ordinary skill in the art. Examples of reducing agents include, but are not limited to borohydrides, citrates, ascorbates, amines such as 4-aminophenol, oleylamine, trimethylamine, and indole, amino acids such as glycine, tryptophan, and proline, and hydrogen. In preferred embodiments, the reaction mixture is devoid of a supplementary reducing agent.

In some embodiments, the iron oxide nanoparticles are crystalline by PXRD. In some embodiments, the iron oxide nanoparticles comprise crystalline $\gamma$-$Fe_2O_3$ by PXRD. In some embodiments, the iron oxide nanoparticles further comprise other elements besides iron and oxygen which are incorporated into the crystalline $\gamma$-$Fe_2O_3$ or an amorphous phase associated with the iron oxide nanoparticles. When such elements are incorporated into the crystalline $\gamma$-$Fe_2O_3$, they may be referred to as "dopants". In such embodiments, such elements are preferably present in an amount of less than 10 atom %, preferably less than 7.5 atom %, preferably less than 5 atom %, preferably less than 2.5 atom %, preferably less than 1 atom %, preferably less than 0.5 atom %, preferably less than 0.1 atom %, based on a total number of iron atoms. In preferred embodiments, the iron oxide nanoparticles are devoid of crystalline phases which are not $\gamma$-$Fe_2O_3$, measured by PXRD.

In general, the iron oxide nanoparticles can be any shape known to one of ordinary skill in the art. Examples of suitable shapes the iron oxide nanoparticles may take include spheres, spheroids, lentoids, ovoids, solid polyhedra such as tetrahedra, cubes, octahedra, icosahedra, dodecahedra, rectangular prisms, triangular prisms (also known as nanotriangles), nanoplatelets, nanodisks, rods (also known as nanorods), blocks, flakes, discs, granules, angular chunks, and mixtures thereof. In the case of nanorods, the rod shape may be defined by a ratio of a rod length to a rod width, the ratio being known as the aspect ratio. For iron oxide nanoparticles of the current invention, nanorods should have an aspect ratio less than 1000, preferably less than 750, preferably less than 500, preferably less than 250, preferably less than 100, preferably less than 75, preferably less than 50, preferably less than 25. Nanorods having an aspect ratio greater than 1000 are typically referred to as nanowires and are not a shape that the iron oxide nanoparticles are envisioned as having in any embodiments. In preferred embodiments, the iron oxide nanoparticles are substantially spherical. Spherical particles may be described by a measure known as sphericity. Sphericity is a measure of how closely the shape of an object resembles that of a perfect sphere and may be calculated for a particle by taking the ratio of the surface area of a sphere having a volume equal to that of the particle to the surface area of the particle. A perfect sphere has a sphericity of 1. In some embodiments, the iron oxide nanoparticles have a mean sphericity of at least 0.75, preferably at least 0.775, preferably at least 0.80, preferably at least 0.825, preferably at least 0.85, preferably at least 0.875, preferably at least 0.90, preferably at least 0.925, preferably at least 0.95, preferably at least 0.975.

In some embodiments, the iron oxide nanoparticles have a uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of iron oxide nanoparticles having a different shape. As used herein, the term "non-uniform shape" refers to an average consistent shape that differs by more than 10% of the distribution of iron oxide nanoparticles having a different shape. In one embodiment, the shape is uniform and at least 90% of the iron oxide nanoparticles are spherical or substantially circular, and less than 10% are polygonal. In another embodiment, the shape is non-uniform and less than 90% of the iron oxide nanoparticles are spherical or substantially circular, and greater than 10% are polygonal.

In some embodiments, the iron oxide nanoparticles have a mean particle size of 10 to 100 nm, preferably 12.5 to 75 nm, preferably 15 to 60 nm, preferably 17.5 to 50 nm, preferably to 40 nm, preferably 22.5 to 37.5 nm, preferably 25 to 35 nm. In embodiments where the iron oxide nanoparticles are spherical, the particle size may refer to a particle diameter. In embodiments where the iron oxide nanoparticles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass. In some embodiments where the iron oxide nanoparticles have an anisotropic shape such as nanorods, the particle size may refer to a length of the nanorod, a width of the nanorod, or an average of the length and width of the nanorod. In some embodiments, the particle size refers to the diameter of a sphere having an equivalent volume as the particle.

In some embodiments, the iron oxide nanoparticles are monodisperse, having a coefficient of variation or relative standard deviation, expressed as a percentage and defined as the ratio of the particle size standard deviation ($\sigma$) to the particle size mean ($\mu$) multiplied by 100 of less than 25%, preferably less than 10%, preferably less than 8%, preferably less than 6%, preferably less than 5%, preferably less than 4%, preferably less than 3%, preferably less than 2%. In some embodiments, the iron oxide nanoparticles of the present disclosure are monodisperse having a particle size distribution ranging from 80% of the average particle size to 120% of the average particle size, preferably 90-110%, preferably 95-105% of the average particle size. In some embodiments, the iron oxide nanoparticles are not monodisperse.

In general, the particle size may be determined by any suitable method known to one of ordinary skill in the art. In some embodiments, the particle size is determined by powder X-ray diffraction (PXRD). Using PXRD, the particle size may be determined using the Scherrer equation, which relates the full-width at half-maximum (FWHM) of diffraction peaks to the size of regions comprised of a single crystalline domain (known as crystallites) in the sample. In some embodiments, the iron oxide nanoparticles have a mean crystallite size of 10 to 100 nm, preferably 12.5 to 75 nm, preferably 15 to 60 nm, preferably 17.5 to 50 nm, preferably 20 to 40 nm, preferably 25 to 35 nm, preferably 27.5 to 30 nm, preferably 28 to 29 nm. In some embodiments, the crystallite size is the same as the particle size. For accurate particle size measurement by PXRD, the particles should be crystalline, comprise only a single crystal, and lack non-crystalline portions. Typically, the crystallite size underestimates particle size compared to other measures due to factors such as amorphous regions of particles, the inclusion of non-crystalline material on the surface of particles such as bulky surface ligands, and particles which may be composed of multiple crystalline domains. In some embodiments, the particle size is determined by dynamic light scattering (DLS). DLS is a technique which uses the time-dependent fluctuations in light scattered by particles in suspension or solution in a solvent, typically water to measure a size distribution of the particles. Due to the details of the DLS setup, the technique measures a hydrodynamic diameter of the particles, which is the diameter of a sphere with an equivalent diffusion coefficient as the particles. The hydrodynamic diameter may include factors not accounted for by other methods such as non-crystalline material on the surface of particles such as surface ligands, amorphous regions of particles, and surface ligand-solvent interactions. Further, the hydrodynamic diameter may not accurately account for non-spherical particle shapes. DLS does have an advantage of being able to account for or more accurately model solution or suspension behavior of the particles compared to other techniques. In preferred embodiments, the particle size is determined by electron microscopy techniques such as scanning electron microscopy (SEM) or transmission electron microscopy (TEM).

In some embodiments, the iron oxide nanoparticles have a saturation magnetization of 17.5 to 27.5 emu/g, preferably 18 to 25 emu/g, preferably 19 to 24 emu/g, preferably 20 to 23 emu/g, preferably 21 to 22 emu/g, preferably 21.5 emu/g. In some embodiments, the iron oxide nanoparticles have a coercivity less than 250 Oe, preferably less than 225 Oe, preferably less than 200 Oe, preferably less than 175 Oe, preferably less than 150 Oe, preferably less than 125 Oe, preferably less than 100 Oe, preferably less than 75 Oe, preferably less than 50 Oe, preferably less than 25 Oe at 275 to 325 K, preferably 280 to 320 K, preferably 290 to 310 K. In preferred embodiments, the iron oxide nanoparticles are superparamagnetic at 0 to 50° C., preferably 10 to 40° C., preferably 15 to 38° C., preferably 20 to 30° C. In some embodiments, the iron oxide nanoparticles are superparamagnetic at room temperature. A magnetic nanomaterial may be characterized by its blocking temperature, the temperature at which the magnetic behavior of the material changes from superparamagnetic to ferromagnetic/ferromagnetic. In some embodiments, the iron oxide nanoparticles have a blocking temperature below 20° C., preferably below 15° C., preferably below 10° C., preferably below 5° C., preferably below 0° C., preferably below −10° C., preferably below −25° C., preferably below −50° C., preferably below −78° C., preferably below −100° C. The magnetic ordering in nanomaterial can be affected by factors such as the composition and particle size. In general, the iron oxide may be of any suitable composition and/or particle size so as to remain superparamagnetic at temperatures at 0 to 50° C., preferably 10 to 40° C., preferably 15 to 38° C., preferably 20 to 30° C.

In some embodiments, the extract comprises at least three selected from the group consisting of: n-hexadecanoic acid, (Z,Z)-9,12-octadecadienoic acid, (Z)-9-octadecenoic acid, octadecanoic acid, (Z)-3-(pentadec-8-en-1-yl)phenol, piperine, 2-(hydroxymethyl)-2-nitro-1,3-propanediol, and tetradecanoic acid. In some embodiments, the extract further comprises at least four selected from the group above. In some embodiments, the extract further comprises at least five selected from the group above. In some embodiments, the extract further comprises at least six selected from the group above. In some embodiments, the extract further comprises at least seven selected from the group above. In some embodiments, the extract further comprises at least eight selected from the group above. In some embodiments, the extract further comprises all of the members of the group above.

In some embodiments, the extract further comprises at least one selected from the group consisting of: quercetin, kaempferol, cappariloside A, capparine A, capparine B, capparisine A, capparisine B, capparisine C, lactucin, lactucopicrin, aesculetin, aesculin, cichoriin, umbelliferone, scopoletin, 6,7-dihydrocoumarin, solasodine, solanine, emodin, cassiollin, *cassia* occidentanol I, *cassia* occidentanol II, arjunin, arjunic acid, arjungenin, arjunetin, arjunone, arjunoside I, arjunoside II, arjunoside III, arjunoside IV, archilletin, achilleine, apigenin, luteolin, tamarixin, tamarixetin, 4-methylcoumarin, and troupin. In some embodiments, the extract further comprises at least two selected from the group above. In some embodiments, the extract further comprises at least three selected from the group above. In some embodiments, the extract further comprises at least four selected from the group above. In some embodiments, the extract further comprises at least five selected from the group above. In some embodiments, the extract further comprises at least six selected from the group above. In some embodiments, the extract further comprises at least seven selected from the group above. These chemicals, as well as others not named here, which are present in the extract of the plant mixture may be referred to collectively as "extract phytochemicals".

In some embodiments, the extract phytochemicals act as surface ligands for the iron oxide nanoparticles. In some embodiments, the extract phytochemicals act as surface ligands by binding non-oxidatively to a surface of the iron oxide nanoparticles. Such non-oxidative binding may occur through, for example, non-deprotonated alcohol, ether, amine, amide, carboxyl, carbonyl, thiol, disulfide, ester, or other functional group acting as an "L-type" ligand and/or physisorption, This binding is distinct from oxidative binding seen in, for example, carboxylates, alkoxides, hydroxide ions or halides, which may act as "X-type" ligands. The non-oxidative binding may occur through metal-ligand coordination type interactions between appropriate functional groups on the extract phytochemicals. The alcohol groups should exist in alcohol form, that is, bearing the hydroxyl proton. Such a form is distinct from the deprotonated alkoxide form. Additionally, there may be non-chemical interactions which cause physisorption of the extract phytochemicals to the surface of the iron oxide nanoparticle. Examples of such non-chemical interactions include electrostatic interactions such as ion (or charged species in general)-ion interactions, ion-dipole interactions, or dipole-dipole interactions; and Van der Waals interactions. While the surface of the iron oxide nanoparticle may have a charge, the extract phytochemicals may be present in either charged or uncharged form. The binding of the extract phytochemicals may also occur ionically or oxidatively. Such oxidative binding may occur, for example, through or involving the formation of, surface iron atoms formally in the +3 oxidation state but which are not fully incorporated into the crystalline γ-Fe$_2$O$_3$ or an amorphous iron oxide phase which may be present on the surface of the iron oxide nanoparticle or through a ligand which is acting as an "X-type" ligand. An example of such oxidative binding is through a thiolate, alkoxide, or amide ion (a deprotonated amine derivative not to be confused with the organic functional group commonly depicted as —C(O)NR2).

In some embodiments, the iron oxide nanoparticles further comprise surface ligands which are not present in the extract. In general, the surface ligands may be any suitable surface ligands known to one of ordinary skill in the art. Examples of such surface ligands include, but are not limited to carboxylates (often referred to by their acid forms) such as citrate (citric acid), oleate (oleic acid), amines such as oleylamine, hexadecylamine, octadecylamine, and 1,6-diaminohexane; thiols such as decanethiol, dodecanethiol, and thiol-terminated polyethylene glycol (PEG-SH); lipids, proteins such as albumin, ovalbumin, thrombin, and lactoglobulin, polysaccharides such as chitosan and dextran; phosphines such as trioctylphosphine, trioctylphosphine oxide, and triphenylphosphine; and surfactants such as cetyltrimethylammonium bromide (CTAB). For examples of surface ligands (also called capping ligands or capping agents), see Javed, et. al., Kobayashi, et. al., and Guerrini, et. al. [Javed, R., et. al., Journal of Nanobiotechnology, 2020, 18, article number 172; Kobayashi, K., et. al., Polymer Journal, 2014, 46, 460-468; and Guerrini, L., et. al., Materials, 2018, 11, 1154].

In some embodiments, the iron oxide nanoparticles have a coating. In such embodiments, the iron oxide nanoparticles should be understood to comprise an iron oxide portion and a coating portion. That is, the coating forms an integral part of the iron oxide nanoparticles. In embodiments where the iron oxide nanoparticles have a coating, the "surface of the iron oxide nanoparticle" should be understood to mean a surface of the coating portion, a surface of the iron oxide portion, or both. In some embodiments, the extract phytochemicals are attached to, disposed upon, acting as a surface ligand for, or otherwise interacting with the coating portion of the iron oxide nanoparticle. In some embodiments, the extract phytochemicals are attached to, disposed upon, acting as a surface ligand for, or otherwise interacting with the iron oxide portion of the iron oxide nanoparticle. In such embodiments, the coating should not prevent the extract phytochemicals from direct interaction with the iron oxide portion of the iron oxide nanoparticle. In some embodiments, the coating is porous, the pores allowing for direct interaction of the extract phytochemicals and the iron oxide portion. Alternatively, the coating may be attached to, disposed upon, encapsulating, or otherwise interacting with the extract phytochemicals, which are themselves in direct contact with the iron oxide portion. Such embodiments may be thought of as sandwiching the extract phytochemicals between the iron oxide portion and the coating portion. Examples of materials which may comprise the coating include, but are not limited to silica, lipids, polymers, and carbon nanomaterials. In general, the polymer may be any suitable polymer known to one or ordinary skill in the art. Examples of such suitable polymer include, but are not limited to polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates;

polyacrylonitriles; polyvinylpyrrolidones (crosslinked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrenepolyethylene/butylene-polystyrene (SEBS) copolymer, available as Kraton.® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-, l- and mesa lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; polyolefin elastomers (e.g., santoprene), ethylene propylene diene monomer (EPDM) rubbers, fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above. The coating may be intended to be broken down, degraded, disintegrated, or otherwise removed from the iron oxide nanoparticle in whole or in part. Such removal may cause or coincide with release of the extract phytochemicals from the iron oxide nanoparticle. In preferred embodiments, the iron oxide nanoparticles are substantially free of a coating.

The present disclosure also relates to a method of killing or inhibiting the growth of bacteria and/or fungus, the method comprising exposing the bacteria and/or fungus to the iron oxide nanoparticles. In general, the exposing may be accomplished by any suitable type of exposing known to one of ordinary skill in the art. In some embodiments, the iron oxide nanoparticles may be used as a component in an antibacterial composition. In general, the antibacterial composition may take any suitable form known to one of ordinary skill in the art. Examples of such forms include, but are not limited to a solid, liquid, gel, foam, dispersion, colloid, or other type of mixture. In some embodiments, the nanoparticles are homogenously distributed throughout the volume of the mixture. In some embodiments, the nanoparticles are non-homogenously distributed throughout the volume of the mixture. In some embodiments, the nanoparticles may separate from other components of the mixture and require mixing or redispersion before use.

In some embodiments, the antibacterial composition is intended for use in conjunction with exposure to visible wavelengths of light. In some embodiments, the antibacterial composition has a mode of action that results from the photocatalytic properties of the nanoparticles. In some embodiments, the antibacterial composition is dissolvable or dispersible in water and may form a component of a water purification composition. When used as a component of such a water purification composition, the nanoparticles may be removed from the water or left in the water. In such an application, the nanoparticles may, in addition to acting in the antibacterial composition, also act in another composition such as one that removes other substances from water that may be undesirable.

Iron oxides (red, yellow, and black) are currently approved as "exempt from certification" as direct food additives and are "Generally Recognized as Safe" as indirect food additives by the US FDA and are approved for use as a food additive in the European Union (E172). The antibacterial composition comprising the nanoparticles may find use as a food additive. In some embodiments, the nanoparticles may be added directly to a foodstuff to form an antibacterial composition that comprises the nanoparticles and the components of the foodstuff. In some embodiments, the antibacterial composition is pre-formed from other components before being added to the foodstuff.

Iron oxide is currently a common component in many cosmetics and bath products. The antibacterial composition may also find use in such products. In some embodiments, the antibacterial composition comprising the nanoparticles is such a cosmetic or bath product. In some embodiments, the antibacterial composition is a component of a cosmetic or bath product that shows antibacterial activity. Examples of such cosmetics or bath products include but are not limited to soaps, facial soaps, facial washes, body washes, shampoos, conditioners, deodorants, antiperspirants, combination deodorants/antiperspirants, fragrances, foot powders, hair dyes or colors, makeup, nail products, personal cleanliness products, shaving products, depilatories, skincare products, tanning products, body or face creams, moisturizers, and anti-acne products.

In some embodiments, the antibacterial composition is not intended for bodily contact or ingestion. In some embodiments, the antibacterial composition is intended to be used in a container, pipe, reservoir, or other such vessel intended to store or transport material, or on a surface. In some embodiments the antibacterial composition is designed to be transiently contacted with the vessel or surface and then removed. In some embodiments, the antibacterial composition is designed to be in contact with the vessel or surface for an extended period of time including the lifetime of either the antibacterial composition or the vessel or surface. In some embodiments, the vessel or surface may allow the nanoparticles to be illuminated by visible wavelengths of light.

In some embodiments, the antibacterial composition further comprises a surfactant. A surfactant may be present at a weight percentage in a range of 0.02-10 wt %, preferably 0.1-5 wt %, more preferably 0.5-2 wt %. Examples of surfactants and surfactants types that may be included in the antibacterial composition may be those surfactants/surfactant types described previously.

In one embodiment, the antibacterial composition may further comprise a mutual solvent. A mutual solvent may be present at a weight percentage of 1-20 wt %, preferably 3-15 wt %, more preferably 4-12 wt %. As defined herein, a "mutual solvent" is a liquid that is substantially soluble in both aqueous and oleaginous fluids, and may also be soluble in other well treatment fluids. As defined here, "substantially soluble" means soluble by more than 10 grams mutual solvent per liter fluid, preferably more than 100 grams per liter. Mutual solvents are routinely used in a range of applications, controlling the wettability of contact surfaces before and preventing or stabilizing emulsions.

Examples of the mutual solvent include propylene glycol, ethylene glycol, diethylene glycol, glycerol, and 2-butoxyethanol. In a preferred embodiment, the mutual solvent is 2-butoxyethanol, which is also known as ethylene glycol butyl ether (EGBE) or ethylene glycol monobutyl ether (EGMBE). In alternative embodiments, the mutual solvent may be one of lower alcohols such as methanol, ethanol, 1-propanol, 2-propanol, n-butanol, n-hexanol, 2-ethylhexanol, and the like, other glycols such as dipropylene glycol, polyethylene glycol, polypropylene glycol, polyethylene glycol-polyethylene glycol block copolymers, and the like, and glycol ethers such as 2-methoxyethanol, diethylene glycol monomethyl ether, and the like, substantially water/oil-soluble esters, such as one or more C2-esters through C10-esters, and substantially water/oil-soluble ketones, such as one or more C2-C10 ketones.

In some embodiments, the antibacterial composition may further comprise a buffer. As used herein, a buffer (more precisely, pH buffer or hydrogen ion buffer) refers to a mixture of a weak acid and its conjugate base, or vice versa. Its pH changes very little when a small or moderate amount of strong acid or base is added to it and thus it is used to prevent changes in the pH of a solution. Buffer solutions are used as a means of keeping pH at a nearly constant value in a wide variety of chemical applications. Examples of buffers include, but are not limited to, HEPES buffer, TAPS, Bicine, Glycylglycine, Tris, HEPPSO, EPPS, HEPPS, POPSO, N-ethylmorpholine, TEA (Triethanolamine), Tricine, TAPSO, DIPSO, TES, BES, phosphoric acid, MOPS, imidazole PIPES and the like.

In one embodiment, the antibacterial composition may further comprise other components, such as alcohols, glycols, organic solvents, fragrances, dyes, dispersants, non-buffer pH control additives, acids or bases, water softeners, bleaching agents, foaming agents, antifoaming agents, catalysts, corrosion inhibitors, corrosion inhibitor intensifiers, viscosifiers, diverting agents, oxygen scavengers, carrier fluids, fluid loss control additives, friction reducers, stabilizers, rheology modifiers, gelling agents, scale inhibitors, breakers, salts, crosslinkers, salt substitutes, relative permeability modifiers, sulfide scavengers, fibers, microparticles, bridging agents, shale stabilizing agents (such as ammonium chloride, tetramethyl ammonium chloride, or cationic polymers), clay treating additives, polyelectrolytes, non-emulsifiers, freezing point depressants, iron-reducing agents, other biocides/bactericides and the like, provided that they do not interfere with the antibacterial activity of the nanoparticles as described herein.

In some embodiments, the bacteria and/or fungus is in the form of a biofilm.

In some embodiments, the bacteria is a gram-positive bacteria. In some embodiments, the bacteria is a gram-negative bacteria. In some embodiments, the bacteria is *P. aeruginosa*. In some embodiments, the bacteria is *S. aureus*. In some embodiments, the fungus is *C. albicans*. In some embodiments, the bacteria and/or fungus is at least one selected from the group consisting of *P. aeruginosa*, *S. aureus*, and *C. albicans*.

In some embodiments, the iron oxide nanoparticles have a minimum inhibitory concentration (MIC) for *P. aeruginosa* of 0.60 to 1.5 mg iron oxide nanoparticles per mL, preferably 0.68 to 1.40 mg, preferably 0.75 to 1.35 mg, preferably 0.9 to 1.2 mg, preferably 1.0 to 1.1 mg iron oxide nanoparticles per mL. In some embodiments, the iron oxide nanoparticles have a MIC for *S. aureus* of 0.9 to 2.45 mg, preferably 0.95 to 2.39 mg, preferably 1 to 2.3 mg, preferably 1.25 to 2.15 mg, preferably 1.3 to 2.1, preferably 1.4 to 2.0 mg preferably 1.5 to 1.9 mg, preferably 1.6 to 1.75 mg, preferably 1.65 to 1.70 mg iron oxide nanoparticles per mL. In some embodiments, the iron oxide nanoparticles have a MIC for *C. albicans* of 1.30 to 2.85 mg, preferably 1.36 to 2.80 mg, preferably 1.4 to 2.75 mg, preferably 1.5 to 2.6 mg, preferably 1.6 to 2.5 mg, preferably 1.75 to 2.3 mg, preferably 1.9 to 2.2 mg, preferably 2.0 to 2.1 mg iron oxide nanoparticles per mL.

The present disclosure also relates to a method of treating colon cancer, the method comprising administering to a patient in need of therapy an effective dose of the iron oxide nanoparticles. In general, the administering may be performed by any route known to one of ordinary skill in the art.

In some embodiments, the iron oxide nanoparticles are administered as a pharmaceutical composition comprising the iron oxide nanoparticles. In some embodiments, the pharmaceutical composition further comprises a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the iron oxide nanoparticles of the present invention to affect solubility or clearance of the compound, for example additional surface ligands and/or coatings.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into the digestive system or colon.

Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the iron oxide nanoparticles in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the iron oxide nanoparticles plus any additional desired ingredient from a previously sterile-filtered solution thereof.

Oral compositions generally include an inert diluent or an edible carrier. The oral compositions can be enclosed in gelatin capsules or compressed into tablets. For the purpose of oral therapeutic administration, the iron oxide nanoparticles can be incorporated with excipients and used in the form of tablets, troches, or capsules. Oral compositions can also be prepared using a fluid carrier, wherein the iron oxide nanoparticles in the fluid carrier is applied orally and swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the iron oxide nanoparticles are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the iron oxide nanoparticles are formulated into ointments, salves, gels, or creams as generally known in the art.

The iron oxide nanoparticles can also be prepared in the form of suppositories (e.g., with conventional suppository bases such as cocoa butter and other glycerides) or retention enemas for rectal delivery.

In one embodiment, the iron oxide nanoparticles are prepared with carriers that will protect the iron oxide nanoparticles against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Dosage unit forms include solid dosage forms, like tablets, powders, capsules, suppositories, sachets, troches and losenges as well as liquid suspensions and elixirs. Capsule dosages, of course, will contain the iron oxide nanoparticles within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The dosage forms include dosage forms suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The iron oxide nanoparticles may be conveniently presented in unit dosage form and prepared by any of the methods well-known in the art of pharmacy.

In some embodiments, the iron oxide nanoparticles are administered in an amount sufficient to provide a concentration of 15 to 200 µg, preferably 25 to 175 µg, preferably 50 to 150 µg iron oxide nanoparticles per mL of tumor volume at a colon cancer-containing site.

The examples below are intended to further illustrate protocols for and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

EXAMPLES

Preparations of Aqueous Liv52 Extract (L52E)

Liv52 tablets (Himalaya Herbals, India) were purchased and were crushed in fine powder form using mortar and pestle. About 10 g of fine powder was then suspended in 100 ml of sterile water overnight. The suspensions were then centrifuged and supernatant was collected. The supernatant was further passed through Whatman No. 1 filter paper and finally filtrate was collected and stored at 4° C.

Liv52 Drug Inspired Synthesis of $\gamma$-$Fe_2O_3$ Nanoparticles

In a typical reaction procedure, 30 ml of aqueous solution of Liv52 extracts was added to 70 ml of 1 mM aqueous solutions of ferric chloride hexahydrate ($FeCl_3 \cdot 6H_2O$) for the synthesis of $\gamma$-$Fe_2O_3$ NPs. The reaction mixture was stirred for 60 min at 65° C. Change in color of the mixture indicates the formation of $\gamma$-$Fe_2O_3$ NPs. The obtained suspensions were centrifuged at 10000 rpm and then washed with sterile water and ethanol several times to remove the impurities and finally dried under vacuum to obtain the $\gamma$-$Fe_2O_3$ NPs in powder form.

UV—Vis Spectroscopy and FTIR Analysis

Formation of $\gamma$-$Fe_2O_3$ NPs was carried out and confirmed by using UV—Vis spectroscopy as previously described [Ashraf J M, et. al., Molecular Neurobiology. 2018; 55(9): 7438-52]. FTIR analysis was employed in the spectral region of 400-4000 $cm^{-1}$ to recognize the presence of functional groups in the aqueous extract of polyherbal Liv52 drug that take part in the synthesis and capping of NPs.

Electron Microscopic and EDS Analysis of $\gamma$-$Fe_2O_3$ NPs

Morphological features of the synthesized $\gamma$-$Fe_2O_3$ NPs was investigated by using SEM and TEM as protocol described elsewhere [Ansari M A, et. al., Biomolecules. 2020; 10(2):336]. The $\gamma$-$Fe_2O_3$ NPs were sonicated for 10 min before being used. Further, the elemental composition of Liv52-mediated bioinspired γ-Fe$_2$O$_3$ NPs was carried out by using energy dispersive spectroscopy (EDS; JED-2300 Japan).

XRD Analysis of γ-Fe$_2$O$_3$ NPs

The crystalline structure and particle size of the powdered NPs was determined using an XRD machine as described in Anasari, et. al. [Ansari M A, et. al., Biomolecules. 2020; 10(2):336].

Vibrating-Sample Magnetometer (VSM) Analysis of γ-Fe$_2$O$_3$ NPs

The measurement of magnetic properties of the synthesized γ-Fe$_2$O$_3$ NPs was performed using a vibrating sample magnetometer at room temperature.

GC-MS Analysis of Liv52 Extract

The investigation of presence of bioactive compounds in methonolic extract of Liv52 was analyzed by GC-MS as protocol described by Ali et al. [Ali S G, et. al., Journal of basic microbiology. 2017; 57(3):193-203].

Antibacterial, Anticandidal and Anti-Biofilm Studies of γ-Fe$_2$O$_3$ NPs

Biofilm-producing strains of multi drug resistant *Pseudomonas aeruginosa* (MDR-PA), Methicillin-resistant *Staphylococcus aureus* (MRSA) and *Candida albicans* were used for antibacterial, anticandidal and antibiofilm study.

Determination of Minimal Inhibitory Concentration (MIC)

Microbroth dilution method was used to determine the MIC of γ-Fe$_2$O$_3$ NPs as described by Balasamy, et. al. [Balasamy R J, et. al., RSC Advances. 2019; 9(72):42395-408]. The bacterial and *Candida* strains treated with two-fold serial dilutions of γ-Fe$_2$O$_3$ NPs (0.156-10 mg/ml) were incubated at 37° C. and 28° C., respectively for overnight. The MIC was defined as the lowest concentration of tested NPs at which no visible growth of the tested bacteria and *Candida* was observed.

Minimal Bactericidal and Fungicidal Concentration (MBC/MFC)

After MIC assessment of γ-Fe$_2$O$_3$ NPs, aliquots of 100 μl from wells in which no visible bacterial and fungal growth was seen were further inoculated on MHA and SDA plates for 24 h at 37° C. and 28° C., respectively. The MBC/MFC endpoint is defined as the lowest concentration of tested NPs that kills 100% population of tested bacterial and Candidal strains.

Effect of γ-Fe$_2$O$_3$ on Biofilm Forming Abilities of MRSA, MDR-PA and *C. albicans*

The inhibition of biofilm formation after treatment with γ-Fe$_2$O$_3$ NPs was quantitatively examined by microtiter crystal violet assay as described by Balasmy, et. al. [Balasamy R J, et. al., RSC Advances. 2019; 9(72):42395-408]. Briefly, fresh cultures of 20 μl of bacteria and yeast (*C. albicans*) were inoculated in 180 μl of different concentrations of synthesized γ-Fe$_2$O$_3$ NPs (0.3125-2.5 mg/ml) and then bacteria were incubated at 37° C. and yeast at 28° C., respectively. MRSA, MDR-PA and *C. albicans* without NPs were considered as control group. After overnight of incubation, the content from the microtiter wells were decanted and gently washed with 1× PBS thrice using ELISA washer and left the microtiter plate for drying. The adhered biofilms was then stained with crystal violet solution (0.1% w/v) for 15 min. After staining, the overflow dyes were decanted and washed again with PBS and dried the wells completely. After drying, the stained biofilm was solubilised with 95% ethyl alcohol and then optical density was taken at 595 nm using ELISA reader.

Visualization of Biofilm Architecture: SEM Analysis

The effect of γ-Fe$_2$O$_3$ NPs on MRSA, MDR-PA and *C. albicans* biofilm architecture was investigated by SEM as described by Jalal, et. al. [Jalal M, Artificial cells, nanomedicine, and biotechnology. 2018; 46(sup1):912-25]. In brief, 100 μl fresh cultures of tested bacterial and yeast strains with and without L52E-γ-Fe$_2$O$_3$ NPs were inoculated on glass coverslips in a 12-wells plate for overnight at 37° C. and 28° C., respectively. After incubation, the glass coverslips were taken off and washed with 1×PBS to remove the unadhered cells. After washing, the coverslips were primarily fixed with glutaraldehyde (2.5% v/v) for 24 h at 4° C. After fixation, washed the coverslips again and then subjected it to dehydration (a series of ethyl alcohol) and drying. After drying, gold coating of treated and untreated samples were performed and then the effects of γ-Fe$_2$O$_3$ NPs on biofilms of tested bacteria and yeast were observed using SEM.

Ultrastructural Alteration in Bacterial and *Candida* Cells Caused by NPs

The ultrastructural changes caused by L52E-γ-Fe$_2$O$_3$ NPs in tested bacterial and yeast strains cells were examined by SEM as protocol described by Shukla et al. [Shukla A K, et. al., Materials Chemistry and Physics. 2019; 233:102-12]. Briefly, ~10$^6$ CFU/ml of MRSA, MDR-PA and *C. albicans* were inoculated in a 2 ml sterile tubes with and without γ-Fe$_2$O$_3$ NPs and then incubated at 24 h at required temperature. After incubation, cells were washed three to four times and fixed with primary fixative glutaraldehyde (4% v/v). After primary fixation, cells were again fixed with secondary fixative i.e., 1% osmium tetroxide for 1 h and then subjected to dehydration (a series of ethanol), drying and gold coating, and then finally observed the effects of NPs on morphology of tested bacteria and *Candida* using SEM at an accelerated voltage of 20 EV.

Evaluation of Anticancer Potential of γ-Fe$_2$O$_3$ NPs

Human colorectal carcinoma cell line (HCT-116 cells) was used to evaluate the anticancer potential of γ-Fe$_2$O$_3$ NPs. 96-well cell culture plates were used for drug treatments using the procedure described by Khan et al. [Khan F A, et. al., Artificial Cells, Nanomedicine, and Biotechnology. 2018; 46(sup3):S247-53]. The cancer cells were treated with different concentrations of γ-Fe$_2$O$_3$ NPs. All the treatments were performed in triplicate for statistical calculations.

MTT Assay

The MTT assay was used to assess and measure the cell metabolic activity and cytotoxicity of γ-Fe$_2$O$_3$ NPs. MTT assay was performed in 96 well culture plates by measuring optical density at 570 nm and cell viability (%) was using equation (1):

$$\% \text{ of cell viability} = \frac{\text{Optical density of nanoparticles} - \text{treated cells}}{\text{Optical density of control cells}} \times 100 \quad (1)$$

Cell Morphology

The effects of different concentrations of γ-Fe$_2$O$_3$ NPs on the anatomy and morphology of Human colorectal carcinoma cell line was analyzed at the end of experiments under an inverted microscope equipped with a digital camera.

Biosynthesis and UV-Vis Analysis of γ-Fe$_2$O$_3$ NPs

Aqueous extract of Liv52, a traditional polyherbal drug was used as a reducing, stabilizing, and capping agent for the synthesis of γ-Fe$_2$O$_3$ NPs. The color of the FeCl$_3$·6H$_2$O after addition of extract change from colourless to dark brown to black precipitates indicated the formation of iron oxide nanoparticles (IONPs). The biosynthesis of γ-$Fe_2O_3$ NPs was confirmed by UV-Vis absorbance spectroscopy which showed a maximum absorbance at 327 nm due to surface plasmon resonance (FIG. 1) and is supported by the results of Balamurughan et al. [Balamurughan M G, et. al., Journal of Chemical and Pharmaceutical Sciences. 2014; 4:201-204]. It has been reported that IONPs shows absorbance peak between 200 to 400 nm [Klačanová. K, et. al., Journal of Chemistry. 2013, Article ID 961629; and Suganya D, et. al., Int J Curr Res. 2016; 8(10:42081-5].

FTIR and GC-MS Analysis

FTIR analysis were performed to identify the possible phytocompounds present in the Liv52 extract that were responsible for the reduction of $Fe^{3+}$ ions and capping as well as stabilization of the reduced iron oxide nanoparticles. The FTIR spectrum of Liv52 extract (FIG. 2) represents the major absorption spectra at 3234 $cm^{-1}$ corresponding to hydroxyl group of polyphenolic compounds, 1633 $cm^{-1}$ corresponds amide group whereas peak 2135 $cm^{-1}$ corresponds to the N—H/C—O stretching vibration (see Balamurughan et al.). The FTIR spectrum of green synthesized IONPs (FIG. 2) represents the shift in peak from 3234 to 3267 $cm^{-1}$, 2135 to 2146 $cm^{-1}$ and 1633 to 1645 $cm^{-1}$ in comparison with the FTIR spectrum of L52E. The peak 638 $cm^{-1}$ indicated the Fe—O vibration of $Fe_2O_3$ nanoparticles, as reported previously which indicated the formation of IONPs [Gotić M, et. al., Materials Research Bulletin. 2009; 44(10):2014-21]. The peak at 1645 cm 1 indicate the presence of carbonyl groups (C═O) of long chain carboxylic fatty acids and polyphenolic compounds present in L52E that might be responsible for the reduction of Fe ions to iron oxide NPs.

Figure 3A:
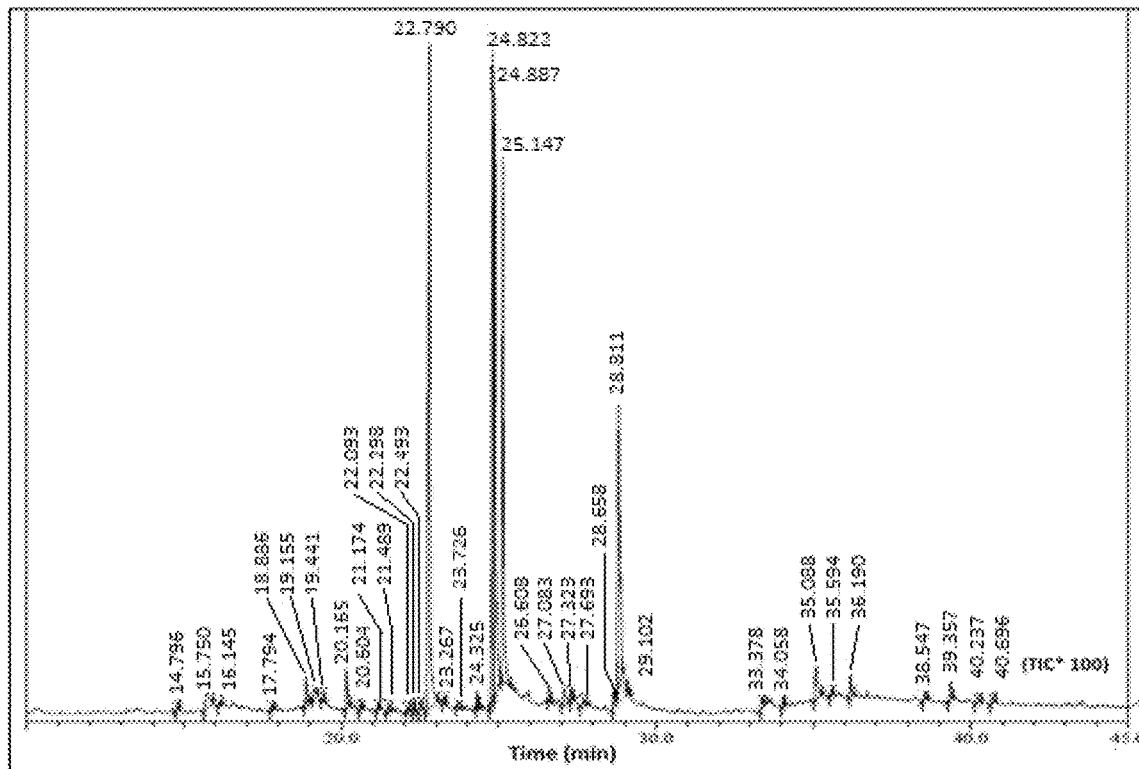
FIG. 3A shows a typical GC-MS chromatogram of the iron oxide nanoparticles synthesized using the extract of the plant mixture indicating 37 peaks of extract phytochemicals associated with the nanoparticles.
Figure 3B:
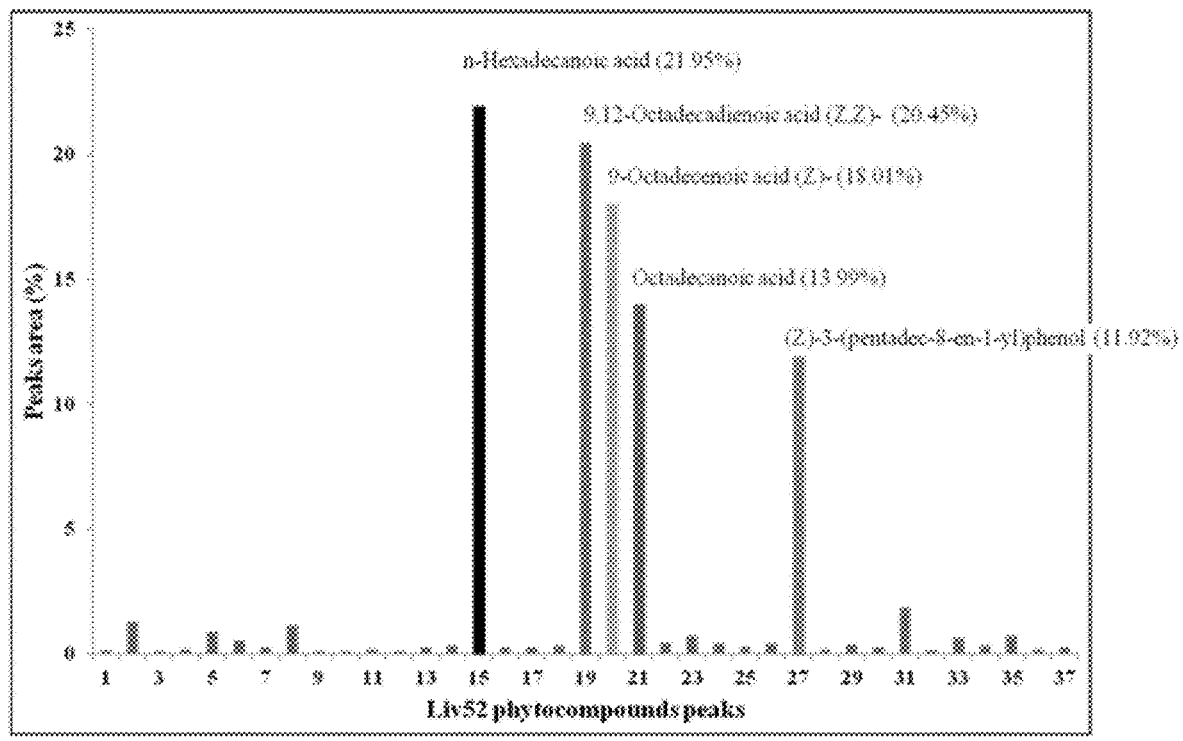
FIG. 3B shows a bar graph showing the major phytochemicals present in the extract.

The GC-MS analysis of L52E was performed to identify and confirm the phytochemicals present in L52E that are responsible for reduction of Fe ions and capping and stabilization of nanoparticles. The GS-MS of L52E shows 37 peaks (FIG. 3A). The major bioactive phytochemicals present in L52E are; n-Hexadecanoic acid (21.95%), 9,12-Octadecadienoic acid (Z,Z)-(20.45%), 9-Octadecenoic acid (Z)-(18.01%), Octadecanoic acid (13.99%), (Z)-3-(pentadec-8-en-1-yl)phenol (11.92%), Piperine (2.22%), 1,3-Propanediol, 2-(hydroxymethyl)-2-nitro-(1.30%) and Tetradecanoic acid (1.14%) on to surface of γ-$Fe_2O_3$NPs could be argued as main bio-fabricating and stabilizing agents (Table. 1; FIG. 3B). It has been suggested that some of these bioorganic moieties of L52E possibly interact with $Fe^{3+}$ ions during the reduction and nucleation process, which ultimately results the formation of nanoparticles [Makarov V V, et. al., Langmuir. 30 (2014) 5982-5988]. It has been suggested that the absorption of L52E on nanoparticle surface was due to ionic interaction, hydrogen bonding, π-π interactions, or reversible bond formation, which provide stability to the bio-fabricated nanoparticles [Silva A B, et. al., Corr. Sci. 48 (2006) 3668-3674; Olivares 0, et. al., Appl. Surf. Sci. 252 (2006) 2894-2909; and Bereket G., Yurt A., Corr. Sci. 43 (2001) 1179-1195]. In addition, it has been observed that some phytocompounds present in L52E contains N, O, Si and P atoms, may also form coatings on metal nanoparticles to protect the nanoparticles from oxidation and corrosion [James A O, Atela A O, Int. J. Pur. Appl. Chem. 3 (2008) 159-163; and Abiola O K., James A O, Corros. Sci. 52 (2010) 661-624]. Recently, Ali et al. have also demonstrated adsorption of organic molecules such as oxime-, methoxy-phenyl ($C_8H_9NO_2$), hexadecanoic acid ($C_{16}H_{32}O_2$), cyclohexanol, 2,6-dimethyl ($C_8H_{16}O$) and ethanone, 1-phenyl ($C_8H_8$) on the surface of hematite (α-$Fe_2O_3$) nanoparticles synthesized by *Aloe vera* extract [Ali K, et. al., Journal of Photochemistry and Photobiology B: Biology. 2018; 188:146-58]. Full results are presented in Table 1 below.

TABLE 1

GC-MS analysis of phytocomponents present in Liv52 extract

| Peak | Retention Time | Peak area (%) | Name of compounds | Mol. weight | Mol. formula | CAS | Class |
|---|---|---|---|---|---|---|---|
| 1 | 14.796 | 0.16 | Octanoic Acid, 3-Oxo-, Methyl Ester | $C_9H_{16}O_3$ | 172 | 22348-95-4 | Methyl ester |
| 2 | 15.750 | 1.30 | 1,3-Propanediol, 2-(hydroxymethyl)-2-nitro- | $C_4H_9NO_5$ | 151 | 126-11-4 | Isobutyl Glycerol, nitro/alkaloid |
| 3 | 16.145 | 0.11 | Benzene, 1-(1,5-Dimethyl-4-Hexenyl)-4-Methyl- | $C_{15}H_{22}$ | 202 | 644-30-4 | aromatic curcumene |
| 4 | 17.794 | 0.17 | 1-Tridecanol | $C_{13}H_{28}O$ | 200 | 112-70-9 | Aliphatic alcohol |
| 5 | 18.886 | 0.86 | Ar-tumerone | $C_{15}H_{20}O$ | 216 | 532-65-0 | aromatic compound ketone |
| 6 | 19.155 | 0.55 | Mome Inositol | $C_7H_{14}O_6$ | 194 | 0-0-0 | carbocyclic sugar |
| 7 | 19.441 | 0.25 | Alpha.-tumerone | $C_{15}H_{22}O$ | 218 | 82508-15-4 | aliphatic ketone |
| 8 | 20.165 | 1.14 | Tetradecanoic acid | $C_{14}H_{28}O_2$ | 228 | 544-63-8 | Fatty acid |
| 9 | 20.604 | 0.10 | 1-Tetradecanol | $C_{14}H_{30}O$ | 214 | 112-72-1 | saturated fatty alcohol |
| 10 | 21.174 | 0.10 | Neophytadiene | $C_{20}H_{38}$ | 278 | 504-96-1 | Alkene compound |
| 11 | 21.489 | 0.19 | Didodecyl phthalate | $C_{32}H_{54}O_4$ | 502 | 2432-90-8 | Aromatic carboxylic acid |
| 12 | 22.093 | 0.09 | 7,9-Di-tert-butyl-1-oxaspiro(4,5)deca-6,9-diene-2,8-dione | $C_{17}H_{24}O_3$ | 276 | 82304-66-3 | Ketone compound |
| 13 | 22.298 | 0.25 | Hexadecanoic acid, Methyl Ester | $C_{17}H_{34}O_2$ | 270 | 112-39-0 | fatty acid methyl esters. |

TABLE 1-continued

GC-MS analysis of phytocomponents present in Liv52 extract

| Peak | Retention Time | Peak area (%) | Name of compounds | Mol. weight | Mol. formula | CAS | Class |
|---|---|---|---|---|---|---|---|
| 14 | 22.493 | 0.33 | 9-Eicosyne | $C_{20}H_{38}$ | 278 | 71899-38-2 | Aliphatic alkyne |
| 15 | 22.790 | 21.95 | n-Hexadecanoic acid (Palmitic acid) | $C_{16}H_{32}O_2$ | 256 | 57-10-3 | saturated fatty acid |
| 16 | 23.267 | 0.25 | Azuleno[4,5-b]furan-2(3H)-one, | $C_{15}H_{18}O_2$ | 230 | 477-43-0 | Ketone compounds |
| 17 | 23.726 | 0.25 | Palmitic Acid, TMS derivative | $C_{19}H_{40}O_2Si$ | 328 | 55520-89-3 | Fatty acid silyl ester |
| 18 | 24.325 | 0.32 | 9,12-Octadecadienoic acid, methyl ester | $C_{19}H_{34}O_2$ | 294 | 2462-85-3 | Ester |
| 19 | 24.822 | 20.45 | 9,12-Octadecadienoic acid (Z,Z)- (Linoleic Acid) | $C_{18}H_{32}O_2$ | 280 | 60-33-3 | polyunsaturated omega-6 fatty acid |
| 20 | 24.887 | 18.01 | 9-Octadecenoic acid (Z)-(Oleic acid) | $C_{18}H_{34}O_2$ | 282 | 112-80-1 | monounsaturated omega-9 fatty acid, |
| 21 | 25.147 | 13.99 | Octadecanoic acid (Stearic acid) | $C_{18}H_{36}O_2$ | 284 | 57-11-4 | saturated fatty acid |
| 22 | 26.608 | 0.45 | 1-(4-Hydroxy-3-methoxyphenyl)dec-4-en-3-one | $C_{17}H_{24}O_3$ | 276 | 555-66-8 | Aromatic Phenolic |
| 23 | 27.083 | 0.73 | Z,Z-8,10-Hexadecadien-1-ol | $C_{16}H_{30}O$ | 238 | 147240-92-4 | Aliphatic alcohol |
| 24 | 27.323 | 0.42 | 9-Octadecenoic acid (Z)- | $C_{18}H_{34}O_2$ | 282 | 112-80-1 | monounsaturated omega-9 fatty acid, |
| 25 | 27.693 | 0.29 | Phosphonic acid, dioctadecyl ester | $C_{36}H_{75}O_3P$ | 586 | 19047-85-9 | ester |
| 26 | 28.658 | 0.42 | Ginkgol (TMS) | $C_{24}H_{42}OSi$ | 374 | 0-00-0 | Aromatic phenols |
| 27 | 28.811 | 11.92 | (Z)-3-(pentadec-8-en-1-yl)phenol (Cardanol monoene) | $C_{21}H_{34}O$ | 302 | 501-26-8 | Aromatic phenols |
| 28 | 29.102 | 0.17 | Phenol, 3-pentadecyl- | $C_{21}H_{36}O$ | 304 | 501-24-6 | Aromatic phenols |
| 29 | 33.378 | 0.39 | Piperine | $C_{17}H_{19}NO_3$ | 285 | 94-62-2 | alkaloid |
| 30 | 34.058 | 0.26 | Squalene | $C_{30}H_{50}$ | 410 | 111-02-4 | Triterpenes |
| 31 | 35.088 | 1.83 | Piperine | $C_{17}H_{19}NO_3$ | 285 | 94-62-2 | alkaloid |
| 32 | 35.594 | 0.16 | (2E,4E,10E)-N-Isobutylhexadeca-2,4,10-trienamide | $C_{20}H_{35}NO$ | 305 | 943546-13-2 | alkaloid |
| 33 | 36.190 | 0.66 | Doconexent, TBDMS derivative | $C_{28}H_{46}O_2Si$ | 442 | 208714-15-2 | Fatty acid silyl ester |
| 34 | 38.547 | 0.34 | Stigmasta-5,22-dien-3-ol, (3.beta.,22E)- | $C_{29}H_{48}O$ | 412 | 83-48-7 | steroid alcohols |
| 35 | 39.357 | 0.72 | Stigmast-5-en-3-ol, (3.beta.)- | $C_{29}H_{50}O$ | 414 | 83-46-5 | steroid alcohols |
| 36 | 40.237 | 0.19 | 2-Hydroxymethyl-2,6,8,8-tetramethyltricyclo[5.2.2.0(1,6)]undecane | $C_{16}H_{28}O$ | 236 | 137235-47-3 | alcohol |
| 37 | 40.696 | 0.25 | Lupeol | $C_{30}H_{50}O$ | 426 | 545-47-1 | triterpenoid |
|  |  | 100 |  |  |  |  |  |

Electron Microscopic Properties of L52E-γ-$Fe_2O_3$ NPs

Figure 4D:
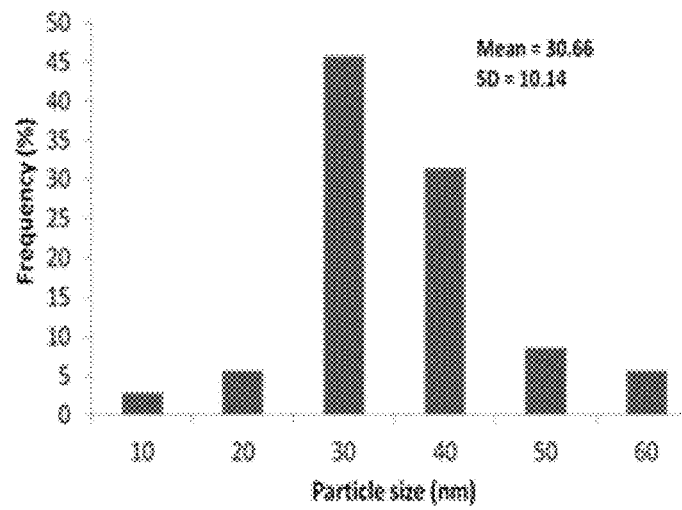

The SEM micrographs revealed that the synthesized nanoparticles were mostly agglomerated and were irregular and spongy in appearance with rough surfaces (FIG. 4A). Further, to confirm the average size, shape and structural morphology of the as-synthesized nanoparticles, the samples were analyzed by TEM. The TEM micrographs clearly shows that the synthesized nanoparticles were well separated, almost uniform in distribution and roughly spherical in shape (FIG. 4B). Particle distribution was analysed by ImageJ software and it was found that the average particles size of the synthesized γ-$Fe_2O_3$ NPs was 30.66 nm (FIG. 4D). In this study, the size of the as-synthesized NPs was found in agreement to the size calculated by XRD analysis (28.52 nm). Further, the elemental composition of synthesized γ-$Fe_2O_3$ NPs was determined by using EDX (FIG. 4C) which shows prominent peak of oxygen (33.95%), chloride (21.45%), silicon (2.87%) and potassium (1.5%) along with three characteristic peaks of Fe (40.23%) at approximate 0.5, 6.5 and 7.0 keV, respectively (FIG. 4C).

XRD Analysis of γ-$Fe_2O_3$ NPs

Figure 5:
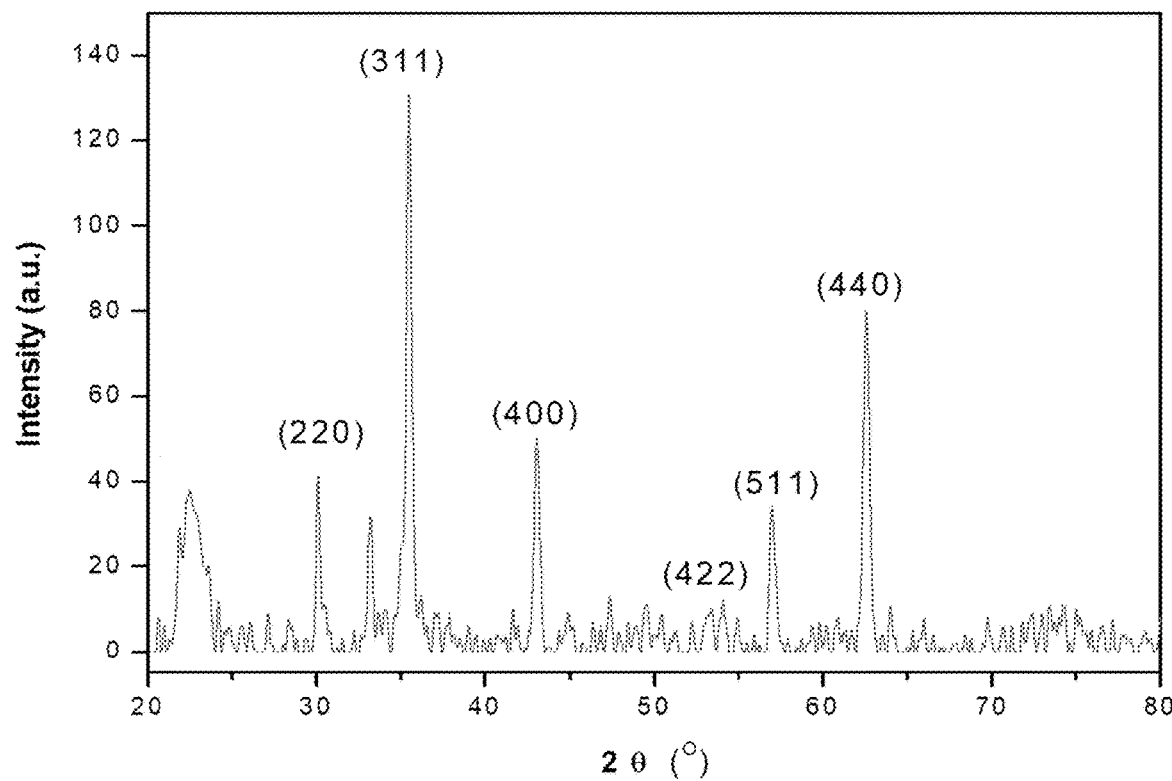
FIG. 5 shows a PXRD pattern of the iron oxide nanoparticles.

The structure and crystallite phase of biosynthesized magnetic nanoparticles annealed at 60° C. was obtained by X-ray diffraction (XRD) in the 2θ range from 20-80° (FIG. 5). It was found that the peaks of as-prepared nanoparticles are in good agreement with the reference data for the JCPDS file (39-1346), and can be indexed to the cubic spinel structure and were identified as maghemite (γ-$Fe_2O_3$) [Wu W, et. al., Science and Technology of Advanced Materials. 2015; 16: 023501 (43 pp), doi:10.1088/1468-6996/16/2/023501; and. Wu W, et. al., Nanoscale Res Lett. 2010; 5(9): 1474-1479]. The main peaks (220), (311), (440), (422), (511) and (440) were observed at 22.44°, 30.15°, 35.46°, 43.12°, 54.20, 57.12° and 62.55°, respectively (FIG. 5), consistent with literature values [Cao D, et. al., Scientific reports. 2016; 6(1):1-9]. The presence of characteristic peaks of γ-Fe$_2$O$_3$ at 30.15° and 43.12° assure the formation of maghemite nanoparticles [Rana P, et. al., Materials Science for Energy Technologies. 2019; 2(1):15-21]. The XRD results also exhibits some unassigned additional peaks which might be due to the presence of bioorganic compounds on the surface of γ-Fe$_2$O$_3$ NPs. They act as reducing and capping agent on the surface of γ-Fe$_2$O$_3$ and also providing the stability to the γ-Fe$_2$O$_3$ NPs. The crystallite size (D) calculated using Scherer's formula was 28.52 nm [Ansari M A, et. al., Biomolecules. 2020; 10(2):336].

Magnetic Properties of Biosynthesized L52E-γ-Fe$_2$O$_3$ NPs

Figure 6:
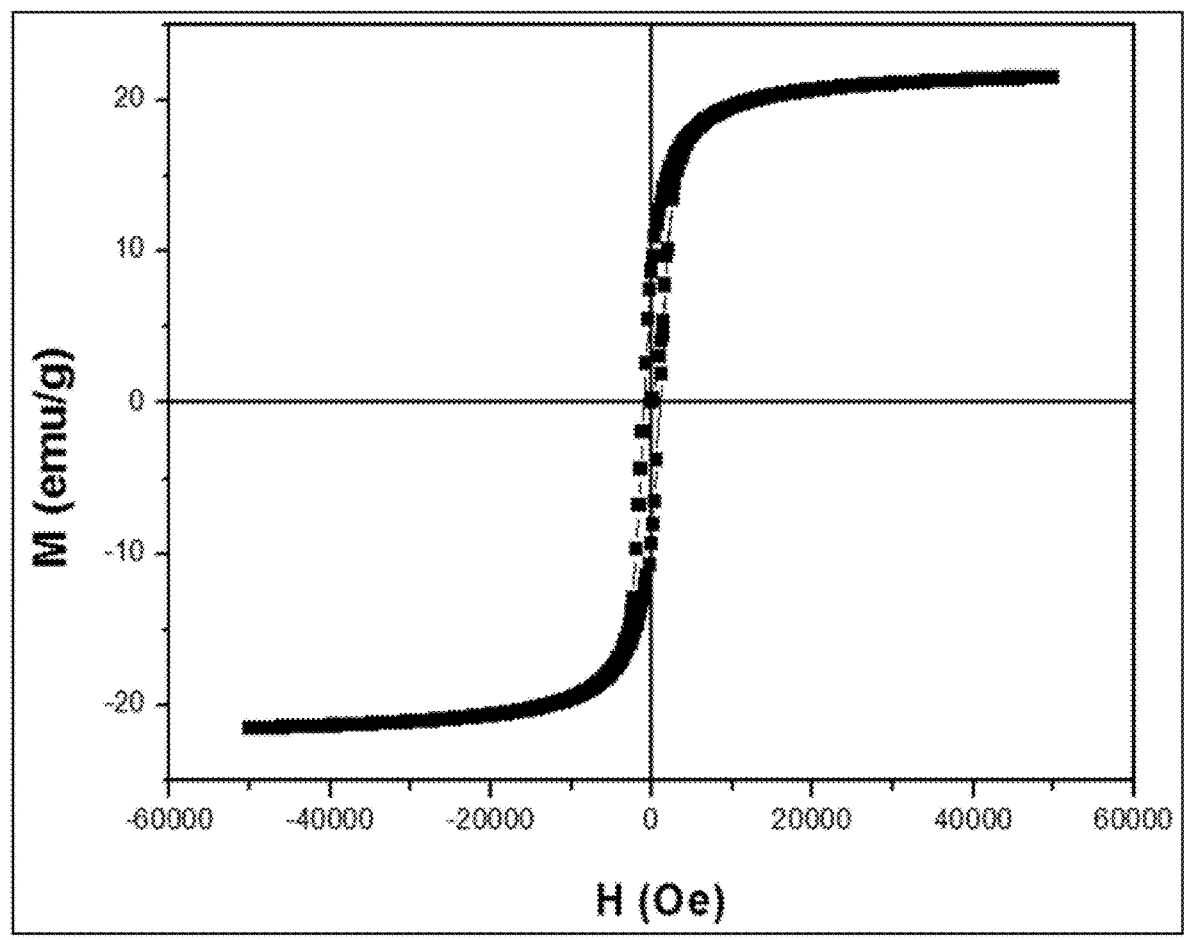
FIG. 6 is a plot of the magnetization vs applied field for the iron oxide nanoparticles.
Figure 6:
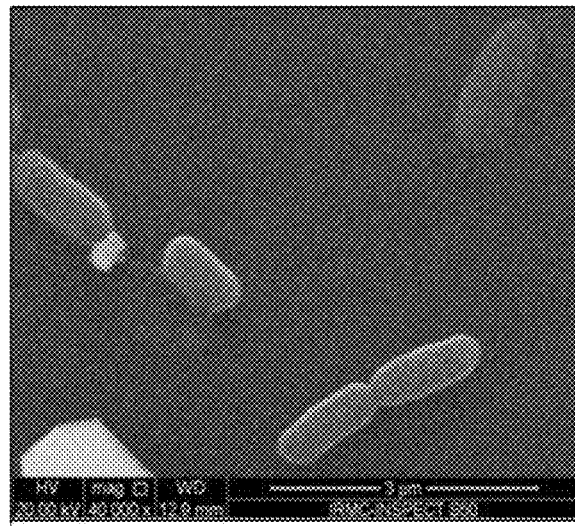
Figure 6:
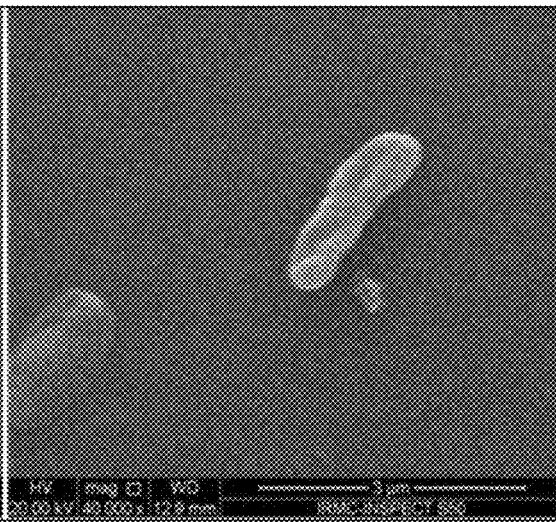

The magnetic behaviour of biosynthesized L52E-γ-Fe$_2$O$_3$ NPs was monitored by measuring hysteresis loop of the Fe$_2$O$_3$ NPs at room temperature (T=300 K). It was found that the L52E-γ-Fe$_2$O$_3$ NPs were superparamagnetic in nature at room temperature with a calculated saturation magnetization (Ms) of 21.5 emu/g (see FIG. 6) which is in accordance to the study of Palanisamy et al. [Palanisamy K L, et. al., Digest Journal of Nanomaterials & Biostructures (DJNB). 2013; 8(2)].

Antibacterial and Anticandidal Activity of L52E-γ-Fe$_2$O$_3$ NPs

The antibacterial and anticandidal activity of L52E-γ-Fe$_2$O$_3$ NPs were investigated against drug resistant gram-negative bacteria *P. aeruginosa*, gram-positive MRSA and *C. albicans* in a 96 well microtiter plate using microbroth dilution method. The MICs values of L52E-γ-Fe$_2$O$_3$ NPs against *P. aeruginosa*, MRSA and *C. albicans* were 1.04±0.36, 1.67±0.72 and 2.08±0.72 mg/ml, respectively. The MBC values for *P. aeruginosa* and MRSA were 2.5 and 3 mg/ml, respectively, while MFC value was found 5 mg/ml against *C. albicans*. The MIC values of L52E-γ-Fe$_2$O$_3$ NPs against *P. aeruginosa*, MRSA and *C. albicans* found are consistent with the study of Farouk et al. [Farouk F, et. al., Biotechnology Letters. 2020; 42(2):231-40]. In a study by Behera, et. al., it has been reported that chemically synthesized IONPs did not show any activity against *P. aeruginosa* (MTTC 1034) at 50 mg/ml [Behera S S, et. al., World J Nano Sci Eng. 2012; 2(4):196-200]. Tran et al. reported that IONPs completely inhibit the *S. aureus* growth at 3 mg/ml [Tran N, et. al., International journal of nanomedicine. 2010; 5:277]. In another study, MIC for MRSA and *P. aeruginosa* was 360±160 and 100±50 µg/ml, respectively [Masadeh M M, et. al., Cytotechnology. 2015; 67(3):427-35]. Prodan et al. reported that IONPs did not exhibit any inhibitory effect on *Candida krusei* and *B. subtilis* growth at 5 mg/ml of concentration [Prodan A M, et. al., Journal of Nanomaterials. 201; 2013 Article ID 893970]. The MIC for different species of bacterial and Candidal strains may differ as well because of their cell wall structures. It was found that gram negative bacteria were more susceptible when compared to gram positive bacteria and yeast. Previous studies also indicate that gram-negative bacteria were more sensitive to IONPs than gram-positive bacteria [Prabhu Y T, et. al., International Nano Letters. 2015; 5(2):85-92; and Salem D M, et. al., The Egyptian Journal of Aquatic Research. 2019; 45(3):197-204]. The present data suggest that biosynthesized γ-Fe$_2$O$_3$ NPs can be used as antimicrobial coatings or therapeutic agents.

Figure 7C:
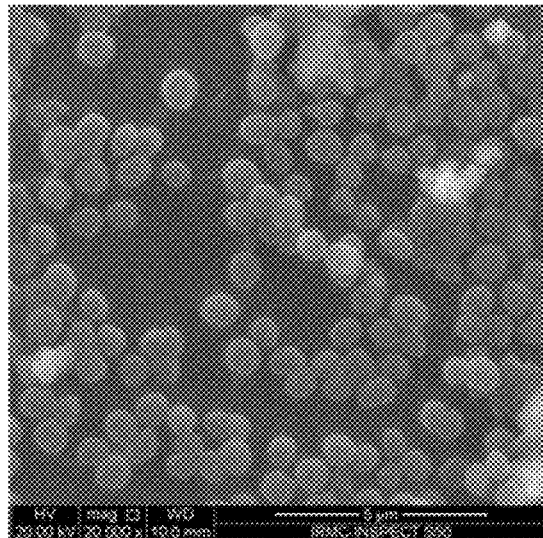
Figure 7D:
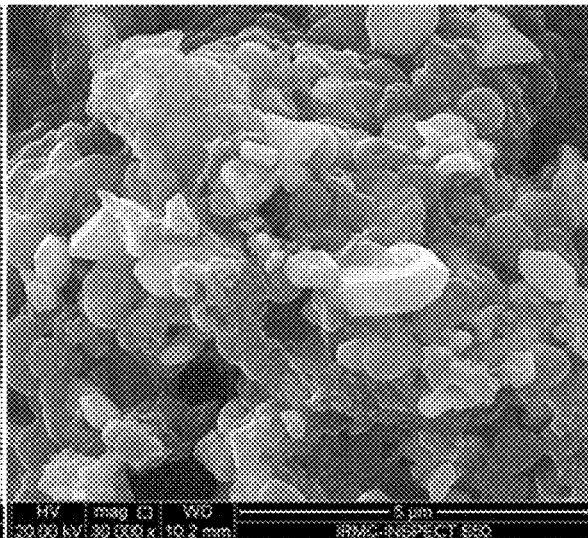
Figure 7E:
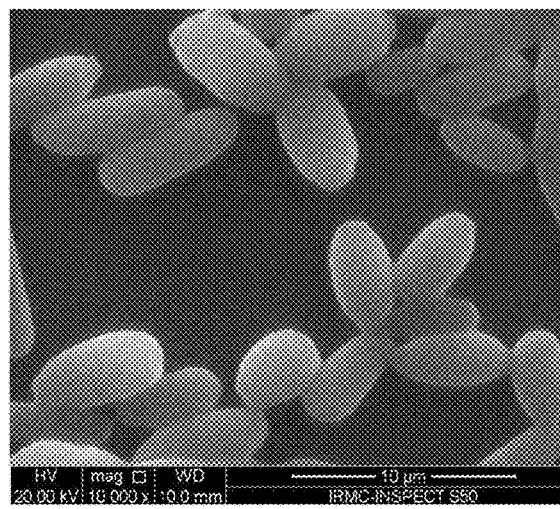
Figure 7F:
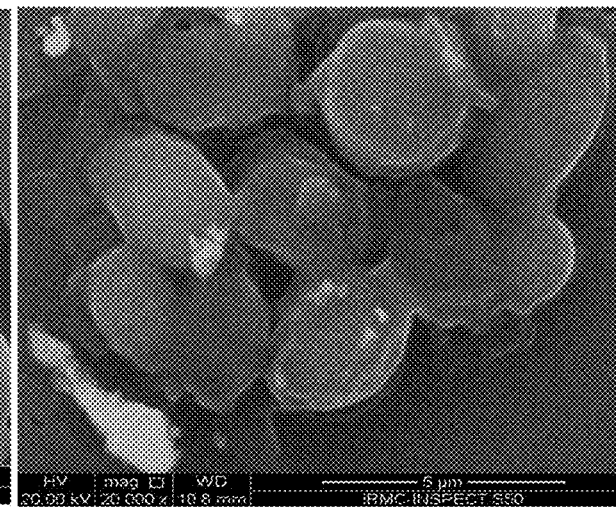

Interaction of L52E-γ-Fe$_2$O$_3$ NPs with bacterial and Candidal cells: SEM analysis SEM was employed to visualize the effects of L52E-γ-Fe$_2$O$_3$ NPs on the ultrastructure of *P. aeruginosa* (FIG. 7A-7B), MRSA (FIGS. 7C-7D), and *C. albicans* (FIG. 7E-7F). The untreated gram-negative *P. aeruginosa* were intact, normal, smooth, and typically rod shaped (FIG. 7A). However, L52E-γ-Fe$_2$O$_3$ NPs treated *P. aeruginosa* cells were severely damaged. The surface of cell envelope were abnormal in appearance and characterized by deep depression and "pits (FIG. 7B). Further, the cells became large, swollen, and elongated that indicate the loss of membrane integrity and severe damage of cell wall.

In case of gram-positive MRSA, it was found that control cells were normal, intact and typically spherical in shape (FIG. 7C). However, L52E-γ-Fe$_2$O$_3$ NPs treated MRSA cells were severely damaged and were characterized by roughness, irregularities and depression on surface of cell envelope (FIG. 7D). The ultrastructural alteration in gram-negative and gram-positive bacteria as analysed by SEM shows that L52E-γ-Fe$_2$O$_3$ NPs were more effective against gram-negative bacteria as compared to gram-positive bacteria. This is possibly due to structural differences in cell wall of both types of bacteria. The cell wall of gram-positive bacteria are mainly composed of a rigid and thick peptidoglycans (20-80 nm) layers that give additional protection and less anchoring moieties for NPs. In contrast, gram-negative cell wall is composed of a thin layer of peptidoglycan i.e., 7-8 nm [Madigan, M., Martinko, J., 2005. Brock biology of microorganisms, 11th ed. Pearson Prentice Hall, New Jersey] but highly negatively charged lipopolysaccharides layer [Salton, M. R. J., Kim, K. S., Baron, S., 1996. Medical microbiology, fourth ed. University of Texas Medical Branch, Galveston] that most likely attracts the positively charged NPs.

The control *C. albicans* cells in the absence of L52E-γ-Fe$_2$O$_3$ NPs displayed normal morphological characteristics with a typical oval shape structure and intact cell membrane and cell-wall (FIG. 7E). In contrast, *C. albicans* cells treated with L52E-γ-Fe$_2$O$_3$ were severely damaged and cells were became round and enlarged, with significant alterations in cell membrane and cell-wall. Roughness and depressions on cell surface has been observed that indicate the loss of integrity of cell membrane and cell-wall (FIG. 7F). It is well known that the cell wall of *C. albicans* play an important role in adhesion and morphogenetic conversions and pathogenicity. The cell wall of *C. albicans* mainly is composed of glucans, chitin and mannoproteins that provide rigidity to the overall cell wall structure [Chaffin W L, et. al., Mol Biol Rev. 1998; 62:130-180]. FIG. 7E shows that untreated yeast cells have distinctive cell wall and cell membrane, but cells treated with L52E-γ-Fe$_2$O$_3$ NPs shows separation of cell membrane from the cells and it was difficult to distinguish cell wall (FIG. 7F). SEM image clearly shows that the interaction of NPs lead to damage of the outer cell wall. These results are consistent with previous reports, where authors reported that formation of pits and hole by NPs in yeast cell lead to the death of *C. albicans* [Lara H H, et. al., Journal of nanobiotechnology. 2015; 13(1): 1-2].

The exact mechanism of antimicrobial action of IONPs is still not clear and understood. It has been reported that the microbiocidal activity of IONPs is due to generation of reactive oxygen species (ROS), such as hydrogen peroxide (H$_2$O$_2$), singlet oxygen ($^1$O$_2$), superoxide radicals (O$_2^-$), or hydroxyl radicals (—OH), which can damaged the proteins and DNA in the bacteria [Rudramurthy G R, et. al., Molecules. 2016; 21(7):836]. Armijo et al. hypothesized that IONPs generate H$_2$O$_2$ which can penetrate the bacterial cell membrane and entered inside the intracellular space that results the death of bacteria [Armijo L M, et. al., Journal of Nanobiotechnology. 2020; 18(1):1-27]. Bertini et al. hypothesized that ROS generated by iron NPs may damage ferredoxins, succinate dehydrogenase, nicotinamide adenine dinucleotide dehydrogenase, hydrogenases, coenzyme Q and nitrogenise [Bertini I, et. al., Bioinorganic chemistry.

Mill Valley: University Science Books; 1994]. Henle, et. al. and Touati both reported the Fenton reaction mechanism for the antibacterial effects of iron oxide which is linked to DNA damage and other macromolecules by production of superoxide anion ($O^{-2}$) and $H_2O_2$ free radicals [Henle E S, Linn S. J Biol Chem. 1997; 272(31):19095-8; and Touati, D., Biochem Biophys. 2000; 373(6), 1-6]. Prabhu et al. also reported that ROS produced by IONPs causes the inhibition of *S. aureus, E. coli, P. vulgaris* and *Xanthomonas* [Prabhu Y T, et. al., International Nano Letters. 2015; 5(2):85-92.]. Lee et al. reported that nano scale zero-valent iron NPs may penetrate the *E. coli* membrane and interact with intracellular oxygen and thus produce oxidative stress that ultimately interferes to bacterial cell membrane [Lee, C., et. al., Environ Sci Technol. 2008; 42(13), 4927-4933]. Rezaei-Zarchi et al. reported that the antimicrobial activity of NPs was possibly due to electromagnetic attraction between the positive charges of NPs and the negative charges of microbe's cell wall and membranes, which oxidize and kill these microbes [Rezaei-Zarchi S, et. al., Iran. J. Pathol. 2010; 5:83-89]. However, Li, et. al. reported that the death of bacteria by IONPs was due the penetration and interlization of NPs inside the bacterial cell that lead to formation of intracellular vacuole, swelling, rupturing and separation of the cell membrane [Li Y, et. al., Molecules. 2018; 23(3): 606].

Figure 8:
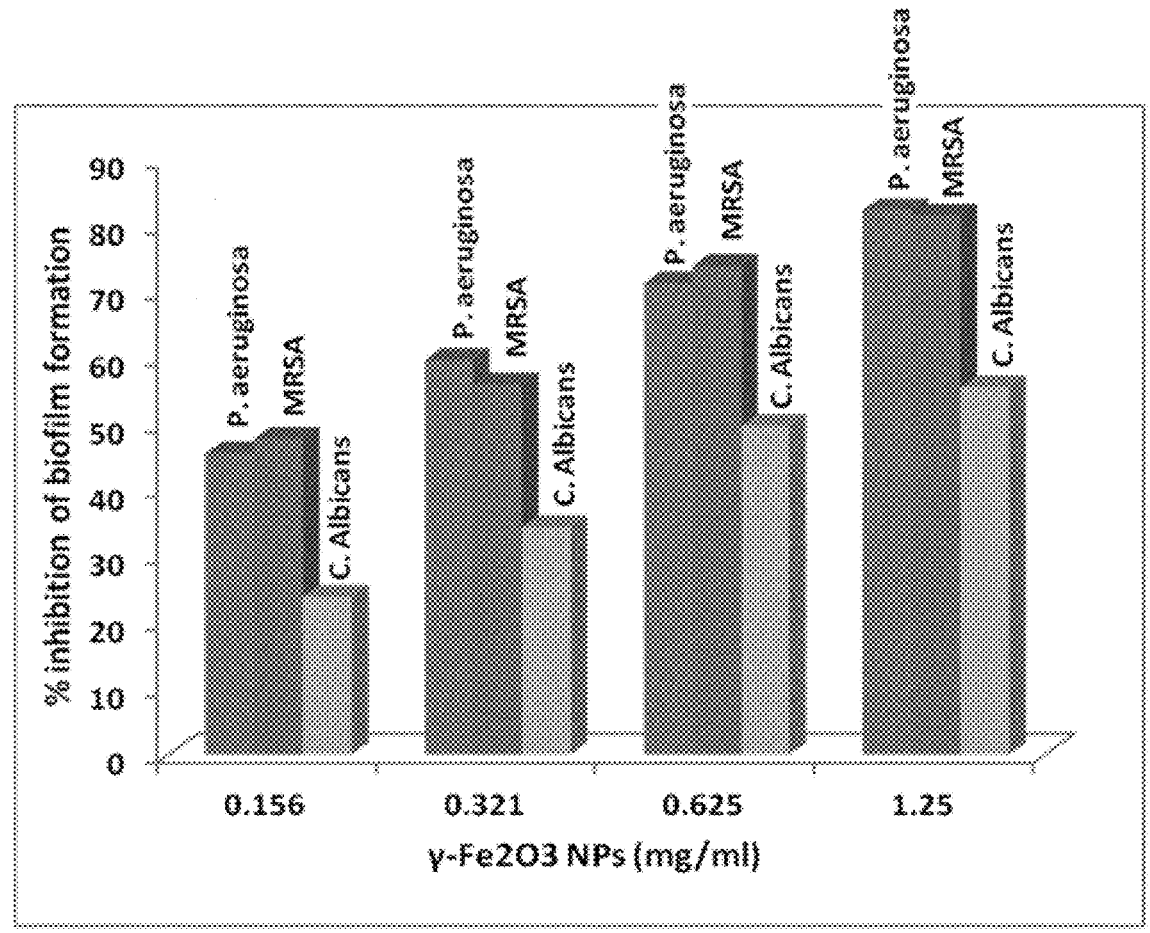
FIG. 8 is a bar graph depicting the dose dependent inhibition of biofilm formation for *P. aeruginosa*, MRSA and *C. albicans* exposed to the iron oxide nanoparticles.
Figure 8:
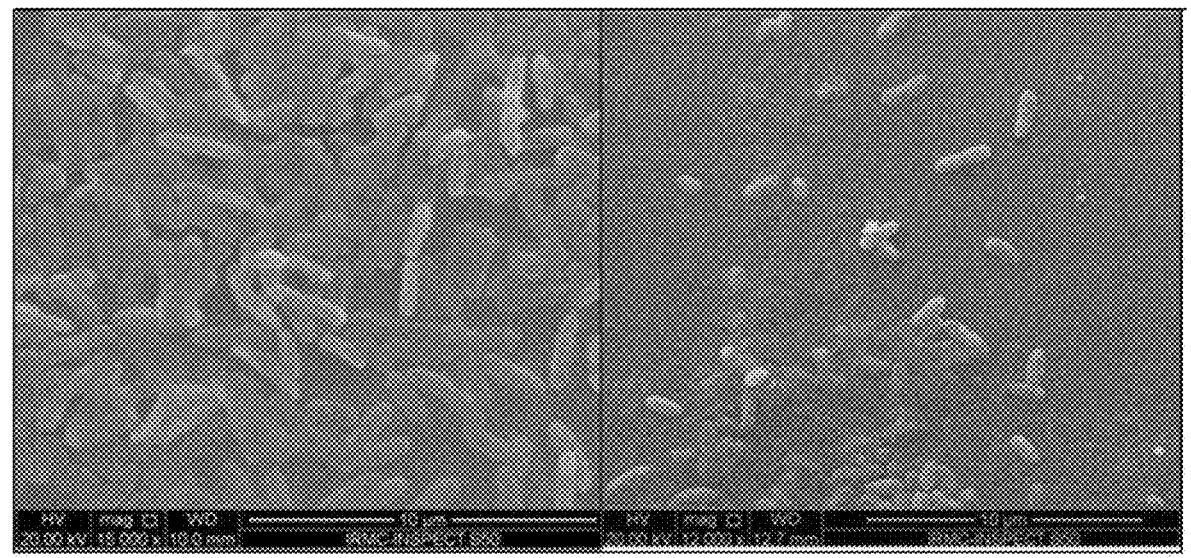

Effects of L52E-γ-$Fe_2O_3$ NPs on Adherence of MRSA, *P. aeruginosa* and *C. albicans* Biofilms The antibiofilm activity of L52E-γ-$Fe_2O_3$ NPs against biofilm forming MRSA, multidrug-resistant *P. aeruginosa*, and *C. albicans* was assessed by its ability to disrupt biofilms formation and their adhesion grown in 96-well polystyrene plate. FIG. 8 clearly shows that L52E-γ-$Fe_2O_3$ NPs inhibit biofilms formation by MRSA, *P. aeruginosa* and *C. albicans* in a dose dependent manner [Shi S F, et. al., International journal of nanomedicine. 2016; 11:6499]. At concentration of 1.25 mg/ml, the inhibition of biofilms formation by L52E-γ-$Fe_2O_3$ NPs was 82.3% for multidrug-resistant *P. aeruginosa*, 81.5% for MRSA, and 55.5% for *C. albicans*, respectively (FIG. 8). Obtained results revealed that L52E-γ-$Fe_2O_3$ NPs had an affinity to hinder the biofilms formation by hampering their adhesion. The present study is in accordance to study of Ali, et. al., where they reported that IONPs inhibit biofilm formation in *P. aeruginosa* by 84.13±6.0 at 1 mg/ml [Ali K, et. al., Journal of Photochemistry and Photobiology B: Biology. 2018; 188:146-58]. Taylor and Webster showed that IONPs in a concentration range of 0.01 to 2 mg/mL were able to kill up to 25% of 48 h old *S. epidermidis* biofilm [Taylor E N, Webster T J, International journal of nanomedicine. 2009; 4:145]. Prodan et al. reported that IONPs at 5 mg/mL exhibited a strong stimulatory effect on the biofilm development by *P. aeruginosa* 1397, *E. faecalis* ATCC 29212, *B. subtilis, E. coli* ATCC 25922, and *C. krusei* 963 [Prodan A M, et. al., J Nanomater. 2013; 2013:587021]. In another study, it has been reported that IONPs significant reduces the biofilm growth in *S. aureus* and *P. aeruginosa* [Sathyanarayanan M B, et. al., International Scholarly Research Notices. 2013; 2013].

Visualization of MRSA, *P. aeruginosa* and *C. albicans* Biofilms by SEM

The effect of L52E-γ-$Fe_2O_3$ NPs at their sub-MIC over matured biofilms, their aggregation and colonization developed on glass surface was investigated by SEM (FIG. 9A-9F). SEM analysis was performed to validate the surface morphology and anatomy of biofilms formed by tested pathogens with or without L52E-γ-$Fe_2O_3$ NPs. L52E-γ-$Fe_2O_3$ NPs treated groups displayed the reduction of thick aggregation of pathogenic bacteria and *Candida* than control (FIG. 9A-9F). This might be due to the degradation/reduction of the thick EPS layer present in the biofilms. Thoroughly, our results have provided altogether evidences that biosynthesised L52E-γ-$Fe_2O_3$ NPs has an effective antibiofilm potential against the different pathogens. The control *P. aeruginosa* biofilms were much aggregated and glass biofilm grown on coverslips surface support higher number of adhered cells that were mostly compact (FIG. 9A), while L52E-γ-$Fe_2O_3$ NPs coated glass surfaces significantly inhibit biofilm formation and their aggregation, clumping and colonization (FIG. 9B). It was observed that *P. aeruginosa* biofilm cells had an irregular and shrivelled appearance. L52E-γ-$Fe_2O_3$ NPs treated group not only hampered biofilm formation but apparent loss of cell wall and membrane was also observed on bacterial surface (FIG. 9B), indicating the severe damage of biofilm integrity and disruption of EPS matrix.

Figure 2:
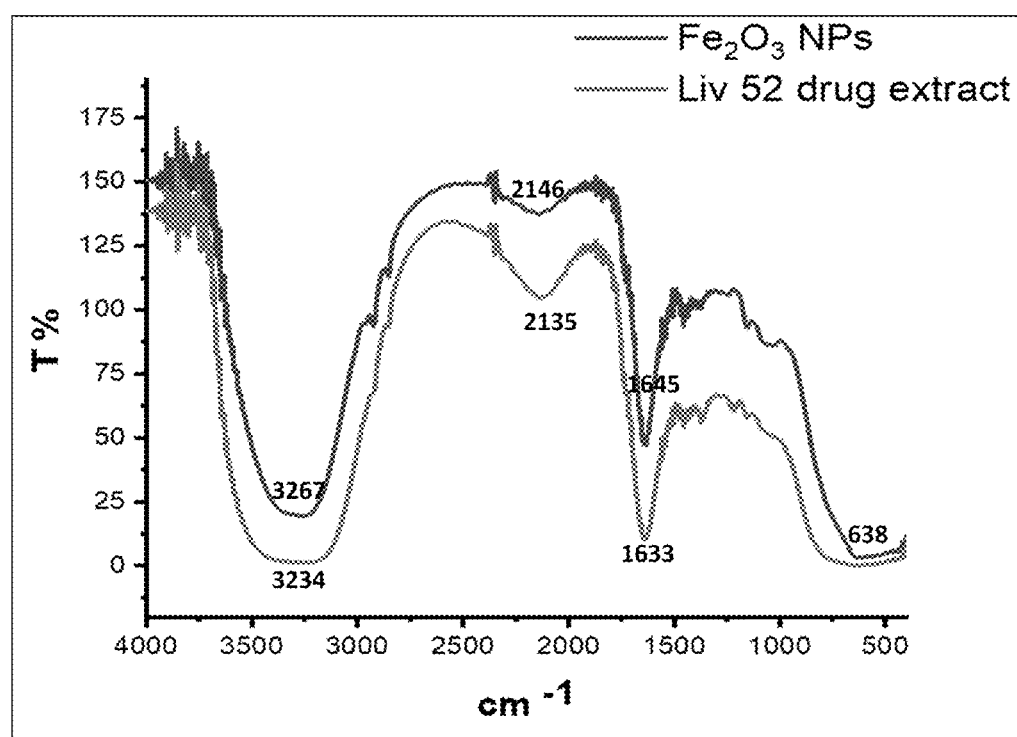
FIG. 2 shows FT-IR spectra of the extract of the plant mixture and the synthesized iron oxide nanoparticles.

Similarly, uncoated control glass coverslips surface support huge number of MRSA biofilm cells colonization, aggregation and their adherence and cells were highly arranged and clumped in chains (FIG. 9C). However, MRSA biofilms treated group shows drastically reduced, scattered and less viable cells (FIG. 9D2). Shi et al. reported that IONPs moderately decreased biofilm formation by *S. aureus* at 0.5 mg/ml, however they reported that at 4 mg/ml, only a small protrusion of biofilm was observed [Shi S F, et. al., International journal of nanomedicine. 2016; 11:6499]. Subbiandoss, et. al. reported that carboxyl-grafted SPIONs cause ~8-fold higher percentage of death of staphylococci biofilm than that of gentamicin [Subbiandoss G, et. al., Acta Biomater. 2012; 8(6):2047-2055].

Biofilm-growing *C. albicans* cultures in the absence of L52E-γ-$Fe_2O_3$ NPs showed a characteristic intense network of hyphae and highly aggregated cells (FIG. 9E). After treatment with L52E-γ-$Fe_2O_3$ NPs scarce biofilms was observed, which were composed predominantly of scattered individual *C. albicans* cells (FIG. 9F). Further, it has been found that the true hyphae were almost absent from these biofilms and thus L52E-γ-$Fe_2O_3$ NPs treatment inhibit hyphae formation and subsequently hampered biofilm formation. Treated biofilm had almost no pseudohyphae or true hyphae, and was clearly reduced in number of cells, disruption of the cell-wall is observed in treated biofilm. Similar results have been reported by Lara et al. against *C. albicans* treated with AgNPs [Lara H H, et. al., Journal of nanobiotechnology. 2015; 13(1):1-2]. It is important to note that hyphae formation and development of biofilms are the two main virulence determinants of *Candida* species [Pierce C G, et. al., Curr Opin Pharmacol. 2013; 13:726-730]. Further, the mature biofilms encased within extracellular matrix also make them resistant to antibiotics [Pierce C G, et. al., Nat Protoc. 2008; 3:1494-1500; and Nett J, et. al., Antimicrob Agents Chemother. 2007; 51:510-520]. The binding of IONPs to cell membranes and/or membrane proteins may also disrupt bacteria functions that may lead to bacterial cell death [Park H, et. al., J Microbiol Methods. 2011; 84(1):41-45].

Anticancer Properties of L52E-γ-$Fe_2O_3$ NPs on Colon Cancerous Cells (HCT-116)

Figure 10:
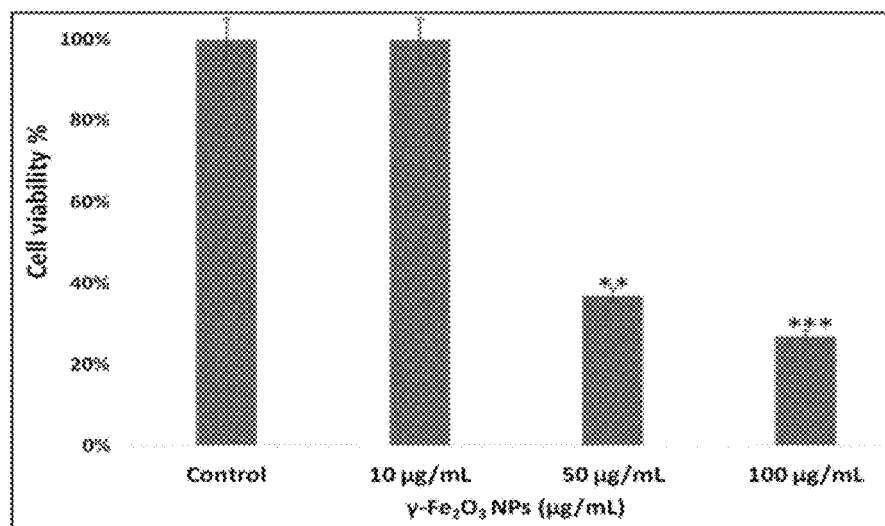
FIG. 10 is a graph of MTT cell viability analysis of HCT-116 cells after treatment with the iron oxide nanoparticles at concentrations of 0, 10, 50, and 100 µg/mL.

The effects of L52E-γ-$Fe_2O_3$ NPs on human colorectal cancer (HCT-116) cells was evaluated by both quantitatively (MTT assay) and qualitatively (microscopic) at different concentration i.e., 10, 50 and 100 μg/ml. The lowest dose of L52E-γ-$Fe_2O_3$ NPs (10 μg/ml) exhibit 99.97% cell survivability whereas it was found that the cells survivability was decreased to 36.96 and 27.08% at 50 and 100 μg/ml, respectively (FIG. 10). It has been found that L52E-γ-Fe$_2$O$_3$ NPs affects survivability of human colorectal cancer cells in a dose-dependent manner. Similar result has been reported by Khan et al. on HCT-116 cells after treatment with fluorescent magnetic submicronic polymeric nanoparticles [Khan F A, et. al., Artificial Cells, Nanomedicine, and Biotechnology. 2018; 46(sup3):S247-53]. Bai et al. reported that IONPs did not exhibit any significant cytotoxic effects on viability of colorectal cancer (HT29) cells at 50 μg/ml and they found that cytotoxicity was 26.98% [Bai A J, et. al., Artificial Cells, Nanomedicine, and Biotechnology. 2018; 46(7):1444-51]. However, in this work, the cytotoxicity was 63.04 and 72.92% at 50 and 100 μg/ml, respectively (FIG. 10). In another study, it has been reported that IONPs (Fe$_3$O$_4$) synthesized by peel extract of Punica Granatum did not exhibit any effects on HCT-116 cells (IC50>250 μg/ml) [Yusefi M, et. al., Journal of Molecular Structure. 202015; 1204:127539].

Impact of L52E-γ-Fe$_2$O$_3$ NPs on the Cell Morphology of HCT-116

Figure 11A:
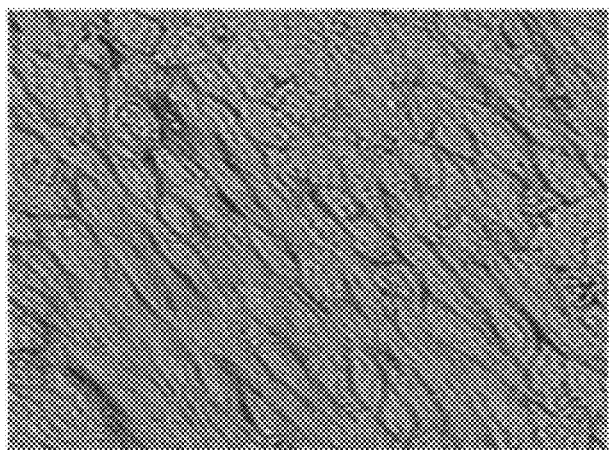
FIGS. 11A-11D are light microscopy images showing the morphology of HCT-116 cells 72 h after exposure to the iron oxide nanoparticles at concentrations of 0, 10, 50 and 100 µg/mL as well as arrows indicating cell dead cell debris.
Figure 11B:
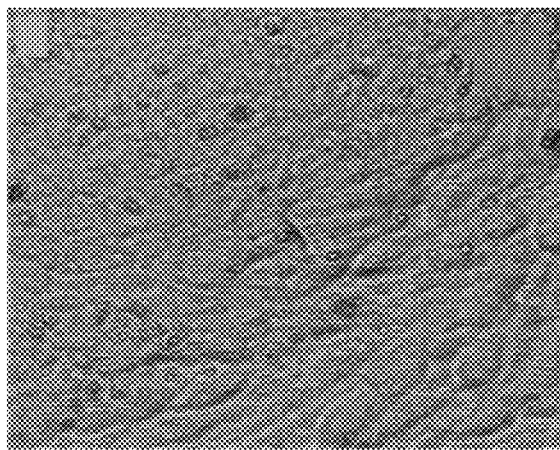
Figure 11C:
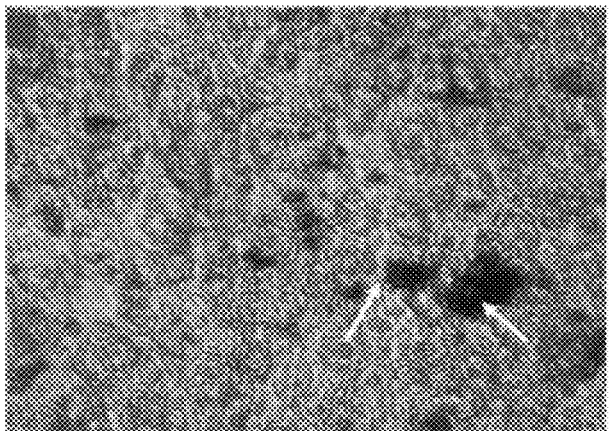
Figure 11D:
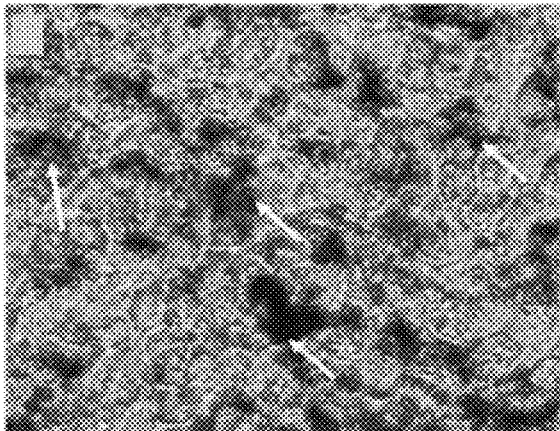

Further, the morphology of HCT-116 cells after 72 h post-treatments of L52E-γ-Fe$_2$O$_3$ NPs was examined qualitatively using light microscopy. The morphology of untreated i.e., control cells were normal and healthy and no damage has been observed (FIG. 11A). The cells treated with low concentration of L52E-γ-Fe$_2$O$_3$ NPs (i.e., 10 μg/mL) did not show any significant anatomical and morphological changes and the cell membrane and nucleus was healthy and normal (FIG. 11B). Whereas HCT-116 cells treated at 50 μg/mL and 100 μg/mL of L52E-γ-Fe$_2$O$_3$ NPs showed significant morphological structural changes in cell membrane and nucleus that includes nuclear condensation nuclear disintegration, and cell death (FIG. 11C-11D). Morphological analysis revealed that L52E-γ-Fe$_2$O$_3$ NPs produced dose-dependent effects on HCT-116 cancer cells. It has been reported that IONPs did not have significant toxic effect on morphology of colorectal cancer (HT29) cells at 100 μg/mL [Bai Aswathanarayan J, et. al., Artificial Cells, Nanomedicine, and Biotechnology. 2018; 46(7):1444-51]. These results are in good agreement with the previous reports which showed that niobium substituted cobalt-nickel nano-ferrite cause similar cytotoxic effects on HCT-116 cells [Tombuloglu H, et. al., Journal of Biomolecular Structure and Dynamics. 2020; 3:1-9]. Khan et al. reported that fluorescent magnetic submicronic polymeric nanoparticles causes' significant nuclear condensation and fragmentation and loss of cell numbers to HCT-116 cells and they also observed that many dead cells and their debris were present in culture media. Though, the exact mechanism of killing of cancerous by IONPs is still unclear. It has been reported that the anticancer IONPs might be because of breakdown of IONPs and subsequent release of Fe ions could be one of probable mechanism of action of IONPs [Singh N, et. al., Nano Rev. 2010: 1:1-15]. Liu et al. and Bai et al. reported that the killing of cancerous cells might be due the production of reactive oxygen species by IONPs or hyperthermia [Liu G, et. al., Small 2013; 446(9):1533-1545]. However in other several studies it has been reported that the probable mechanisms of killing of cancer cells by IONPs could be due loss of membrane integrity, DNA damage, arrest of cell cycle, and cell apoptosis [Feng, Q, et. al., Sci. Rep. 2018; 8:2082; Liu, Y, et. al., Nanotechnology 2014; 25 (449): 425101; Chen, J, et. al., Biomaterials. 2015; 71: 168-177; and Palanisamy, S, et. al., Dalton Trans. 2019; 2(48): 9490-9515]. It has been reported that the paramagnetic and supermagnetic IONPs showed anticancer activity when applied near-infrared or oscillating magnetic fields [Laurent S, et. al., Adv Colloid Interface Sci. 2011; 166:8-23.]. Orel et al. reported that the antitumor effect of anticancer drug doxorubicin enhanced when complex with magnetic Fe$_3$O$_4$ NPs [Orel V, et. al., Nanomedicine. 2015; 11:47-55]. Several studies reported that IONPs has been widely applied in magnetic tumor hyperthermia along with radiotherapy or chemotherapy for the treatment of glioblastoma, glioma and prostate cancer [Van Landeghem F K, et. al., Biomaterials. 2009; 30:52-57; Silva A C, et. al., Int J Nanomed. 2011; 6:591-603; Johannsen M, et. al., Int J Hyperthermia. 2010; 26:790-795; and Maier-Hauff K, et. al., J Neurooncol. 2011; 103:317-324]. Due to magnetic property and anticancer activity of synthesized L52E-γ-Fe$_2$O$_3$ NPs in this study, it has been suggested that the anticancer activity of IONPs can be further enhanced by applying external magnetic field alone or in amalgamation with other cancer therapeutics drugs. However, future investigations on the exact killing mechanisms and safety profile of L52E-γ-Fe$_2$O$_3$ NPs on HCT-166 cells and other cancerous cell are warranted.

The invention claimed is:

1. A method of treating a bacterial or fungal biofilm, comprising:
    exposing the biofilm to a treatment composition comprising
        iron oxide nanoparticles, and
        a saline dispersion medium;
        wherein the iron oxide nanoparticles are stabilized with an extract of a plant mixture comprising *Capparis spinosa*, *Cichorium intybus*, *Solanum nigrum*, *Cassia occidentalis*, *Terminalia aijuna*, *Achillea millefolium*, and *Tamarix gallica*, and
        the iron oxide nanoparticles are suspended in the dispersion medium.

2. The method of claim 1, wherein the biofilm comprises *Pseudomonas aeruginosa* (MDR-PA), Methicillin-resistant *Staphylococcus aureus* (MRSA) or *Candida albicans*.

3. The method of claim 2, wherein the iron oxide nanoparticles have a minimum inhibitory concentration (MIC) for *P. aeruginosa* of 0.60 to 1.5 mg iron oxide nanoparticles per mL, a MIC for *S. aureus* of 0.9 to 2.45 mg iron oxide nanoparticles per mL, and a MIC for *C. albicans* of 1.30 to 2.85 mg iron oxide nanoparticles per mL.

4. The method of claim 1, further comprising:
    making the iron oxide nanoparticles by:
    mixing an iron precursor solution comprising an iron (III) salt and water with an extract composition of the plant mixture to form a reaction mixture,
    heating the reaction mixture to form the iron oxide nanoparticles, and
    isolating the iron oxide nanoparticles; then
    mixing the iron oxide nanoparticles with the saline solution to form the treatment composition.

5. The method of claim 4, further comprising:
    soaking the plant mixture in water in an amount of 1 g of plant mixture per 1 to 25 mL of water at 5 to 50° C. for 4 to 48 hours to form a plant suspension, and
    filtering the plant suspension to form the extract composition.

6. The method of claim 4, wherein the plant mixture comprises:
    26 to 27.5 wt % *Capparis spinosa*;
    26 to 27.5 wt % *Cichorium intybus*;
    12.5 to 14 wt % *Solanum nigrum*;
    6 to 7 wt % *Cassia occidentalis*;
    12.5 to 14 wt % *Terminalia arjuna*;
    6 to 7 wt % *Achillea millefolium*; and
    6 to 7 wt % *Tamarix gallica*.

7. The method of claim 4, wherein:
the iron (III) salt is an iron (III) halide; and
the heating is performed at 40 to 80° C. for 15 to 180 minutes.

8. The method of claim 4, wherein the reaction mixture has an iron (III) concentration of 0.25 to 1.25 mM and the extract composition is present in the reaction mixture in an amount of 24 to 120 mL per mmol of iron (III).

9. The method of claim 1, wherein the iron oxide nanoparticles comprise crystalline γ-$Fe_2O_3$ by PXRD and have a mean particle size of 10 to 100 nm by electron microscopy.

10. The method of claim 1, wherein the iron oxide nanoparticles comprise crystalline γ-$Fe_2O_3$ by PXRD.

11. The method of claim 1, wherein the iron nanoparticles have a mean particle size of 10 to 100 nm by electron microscopy.

12. The method of claim 1, wherein the iron nanoparticles have a saturation magnetization of 17.5 to 27.5 emu/g and a coercivity less than 250 Oe at 275 to 325 K.

13. The method of claim 1, wherein the plant mixture comprises:
26 to 27.5 wt % *Capparis spinosa*;
26 to 27.5 wt % *Cichorium intybus*;
12.5 to 14 wt % *Solanum nigrum*;
6 to 7 wt % *Cassia occidentalis*;
12.5 to 14 wt % *Terminalia arjuna*;
6 to 7 wt % *Achillea millefolium*; and
6 to 7 wt % *Tamarix gallica*.

14. The method of claim 1, wherein the extract comprises at least three selected from the group consisting of n-hexadecanoic acid, (Z,Z)-9,12-octadecadienoic acid, (Z)-9-octadecenoic acid, octadecanoic acid, (Z)-3-(pentadec-8-en-1-yl)phenol, piperine, 2-(hydroxymethyl)-2-nitro-1,3-propanediol, and tetradecanoic acid.

15. The method of claim 14, wherein the extract further comprises at least one selected from the group consisting of quercetin, kaempferol, cappariloside A, capparine A, capparine B, capparisine A, capparisine B, capparisine C, lactucin, lactucopicrin, aesculetin, aesculin, cichoriin, umbelliferone, scopoletin, 6,7-dihydrocoumarin, solasodine, solanine, emodin, cassiollin, *cassia* occidentanol I, *cassia* occidentanol II, arjunin, arjunic acid, arjungenin, arjunetin, arjunone, arjunoside I, arjunoside II, arjunoside III, arjunoside IV, archilletin, achilleine, apigenin, luteolin, tamarixin, tamarixetin, 4-methylcoumarin, and troupin.

\* \* \* \* \*